US009598496B2

(12) United States Patent
Kurosawa et al.

(10) Patent No.: US 9,598,496 B2
(45) Date of Patent: Mar. 21, 2017

(54) ANTIBODY CAPABLE OF SPECIFICALLY RECOGNIZING TRANSFERRIN RECEPTOR

(75) Inventors: Yoshikazu Kurosawa, Aichi (JP); Kazuhiro Morishita, Miyazaki (JP); Lilin Zhang, Tokyo (JP); Gene Kurosawa, Aichi (JP); Katsuyuki Mitomo, Tokyo (JP); Yukio Sudo, Tokyo (JP); Fumiko Nomura, Saitama (JP); Yoshinori Ukai, Aichi (JP)

(73) Assignees: PERSEUS PROTEOMICS INC., Tokyo (JP); UNIVERSITY OF MIYAZAKI, Miyazaki-Shi (JP)

( * ) Notice: Subject to any disclaimer, the term of this patent is extended or adjusted under 35 U.S.C. 154(b) by 0 days.

(21) Appl. No.: 14/116,714

(22) PCT Filed: May 7, 2012

(86) PCT No.: PCT/JP2012/061676
§ 371 (c)(1),
(2), (4) Date: Dec. 30, 2013

(87) PCT Pub. No.: WO2012/153707
PCT Pub. Date: Nov. 15, 2012

(65) Prior Publication Data
US 2014/0114054 A1 Apr. 24, 2014

(30) Foreign Application Priority Data

May 9, 2011 (JP) .................. 2011-104007

(51) Int. Cl.
*A61K 39/395* (2006.01)
*C07K 16/28* (2006.01)
*C07K 16/30* (2006.01)

(52) U.S. Cl.
CPC .......... *C07K 16/30* (2013.01); *C07K 16/2881* (2013.01)

(58) Field of Classification Search
None
See application file for complete search history.

(56) References Cited

U.S. PATENT DOCUMENTS

| 2009/0053243 A1 | 2/2009 | Kurosawa et al. |
| 2009/0203538 A1 | 8/2009 | Sugioka et al. |

FOREIGN PATENT DOCUMENTS

| CN | 101245107 A | 8/2008 |
| JP | 2005-185281 A | 7/2005 |
| JP | 2008-508904 A | 3/2008 |
| WO | WO 2005/121179 A2 | 12/2005 |
| WO | WO 2006/090750 A1 | 8/2006 |
| WO | WO 2008/007648 A1 | 1/2008 |

OTHER PUBLICATIONS

Bendig, M.M. Humanization of rodent monoclonal antibodies by CDR grafting. Methods: A Companion to Methods in Enzymology, 1995; vol. 8, p. 83-93.*
Paul, W.E. Fundamental Immunology, 3rd Edition, 1993, pp. 292-295.*
MacCallum R.M. et al, Antibody-antigen interactions: Contact analysis and binding site topography. J. Mol. Biol., 1998, vol. 262, p. 732-745.*
Casset F, et al. A peptide mimetic of an anti-CD4 monoclonal antibody by rational design. Biochemical and Biophysical Research Communications, 2003, vol. 307, p. 198-205.*
Japanese and English version of International Preliminary Report on Patentability (Forms PCT/IB/326, PCT/IB/373, PCT/ISA/237 and PCT/IB/338) issued in PCT/JP2012/061676 on Nov. 21, 2013.
Brooks et al., "Phase la Trial of Murine Immunoglobulin A Antitransferrin Receptor Antibody 42/6", Clinical Cancer Research, vol. 1, Nov. 1995, pp. 1259-1265.
Chinese Office Action for Chinese Application No. 201280022819.7, dated Nov. 28, 2014, with an English translation.
Extended European Search Report for European Application No. 12781761.7, dated Dec. 15, 2014.
Poul et al., "Selection of Tumor-Specific Internalizing Human Antibodies from Phage Libraries", J. Mol. Biol., vol. 301, 2000, pp. 1149-1161.
White et al., "Combinations of Anti-Transferrin Receptor Monoclonal Antibodies Inhibit Human Tumor Cell Growth in Vitro and in Vivo: Evidence for Synergistic Antiproliferative Effects", Cancer Research, vol. 50, Oct. 1, 1990, pp. 6295-6301.
Zhao et al., "Expression, Purification and Activity Analysis of Anti-human Transferrin Receptor ScFv", Chinese Journal of Biotechnology, vol. 22, No. 3, May 2006, with an English abstract.
Zhao et al., "Preparation of the Human Transferrin Receptor and its Special Antibodies", Letters in Biotechnology, vol. 17, No. 4, Jul. 2006, pp. 571-573, with an English abstract.
Zhao et al., "Screening and identification of antibodies against transferrin receptor", Chin J Cell Mol Immunol, vol. 22, No. 5, 2006, pp. 657-659, with an English abstract.
Chinese Office Action for Chinese Application No. 201280022819.7 dated Jul. 29, 2015, with an English translation.
Japanese Office Action which issued in Japanese Patent Application No. 2013-514005 on Feb. 9, 2016.
European Office Action issued in European Patent Application No. 12 781 761.7 on Sep. 2, 2016.

* cited by examiner

*Primary Examiner* — Michael Pak
(74) *Attorney, Agent, or Firm* — Birch, Stewart, Kolasch & Birch, LLP

(57) ABSTRACT

An object of present invention is to provide a complete human anti-human TfR antibody, which specifically recognizes human TfR, inhibits the survival or growth of cancer cells that highly express TfR, and has no immunogenicity to humans. The present invention provides an antibody which specifically reacts with human TfR, wherein the antibody comprises any one of the amino acid sequences shown in SEQ ID NOS: 1-3, 7-9, 13-15, 19-21, 25-27, 31-33, 37-39, 43-45, 49-51, 55-57, 61-63, 67-69, 73-75, 79-81, 85-87, 91-93, 97-99, 103-105, 109-111, and 115-117, as each of a heavy chain first complementarity determining region (VH CDR1), a heavy chain second complementarity determining region (VH CDR2), and a heavy chain third complementarity determining region (VH CDR3).

36 Claims, 4 Drawing Sheets

1. TfR001
2. TfR003
3. TfR005

Human IG Jλ-IG Cλ cluster

ANTIBODY CAPABLE OF SPECIFICALLY RECOGNIZING TRANSFERRIN RECEPTOR

TECHNICAL FIELD

The present invention relates to an anti-TfR antibody specifically reacting with a human TfR antigen. In addition, the present invention relates to a pharmaceutical composition comprising the anti-TfR antibody, and particularly to a pharmaceutical composition associated with the treatment of malignant tumor.

BACKGROUND ART

Cancer is the number one cause of death in Japan, and with aging, the number of patients suffering from cancer has been increasing year by year. Thus, it has been strongly desired to develop a drug or a treatment method, which is highly effective and highly safe. Conventional chemotherapy, radiotherapy and the like have been problematic in that they cause damage to normal cells, in addition to killing cancer cells, and they cause strong side effects. In order to solve this problem, studies have been intensively conducted regarding molecularly targeted therapy, in which a drug targeting a molecule that is expressed specifically in a cancer cell is designed, and the therapy is then carried out using the drug. Among such molecularly targeted cancer therapeutic agents, antibody agents have attracted considerable attention because they are advantageous in terms of their long half-life and a few side effects. Examples of successfully developed cancer therapeutic agents include a chimeric antibody Rituxan that targets CD20 (Non Patent Literature 1), a humanized antibody Herceptin that targets Her2/neu (Non Patent Literature 2), and a humanized antibody Avastin that targets a vascular endothelial growth factor (VEGF). These antibodies have been used for cancer as a target disease, and their therapeutic effects have been recognized.

Antibodies used as therapeutic agents are divided into non-labeled antibodies and labeled antibodies. The action mechanisms of such non-labeled antibodies are considered to be: (1) antibody-dependent cellular cytotoxicity (ADCC) (Non Patent Literature 3) or complement-dependent cytotoxicity (CDC) (Non Patent Literature 4), which are associated with immunocytes or molecules; (2) inhibition of signals associated with intracellular survival or growth by target molecules; (3) induction of apoptosis; and (4) regulation of secretion of cytokines. By combining these mechanisms, the non-labeled antibody kills tumor cells or terminates the growth thereof, so as to exhibit its therapeutic effects. On the other hand, a labeled antibody is formed by linking a radioactive substance or a cytotoxic substance such as a toxin, an enzyme or a drug to an antibody, and the specificity of the antibody is utilized to deliver such a substance only to cancer tissues, so as to achieve the improvement of therapeutic effects and reduction in side effects.

At first, a transferrin receptor (TfR) was identified as a receptor that is present on a reticulocyte as a cell membrane structure for incorporating transferrin (Tf)-bound iron into a cell (Non Patent Literature 5). Thereafter, it was discovered that the transferrin receptor (TfR) is expressed in placental trophoblasts (Non Patent Literatures 10 to 12), in activated lymphocytes (Non Patent Literature 12), and further, in various tumor cells. It has been reported that the transferrin receptor (TfR) is expressed at a high level, for example, in breast cancer (Non Patent Literature 6), prostate cancer (Non Patent Literature 7), lung cancer (Non Patent Literature 8), pancreatic cancer (Non Patent Literature 9), colon cancer (Non Patent Literatures 30 and 31), stomach cancer (Non Patent Literature 31), bladder cancer (Non Patent Literatures 32 and 33), hepatic cancer (Non Patent Literature 34), cervical cancer (Non Patent Literature 35), brain tumor (Non Patent Literature 36), chronic lymphocytic leukemia (Non Patent Literatures 37 and 38), non-Hodgkin's lymphoma (Non Patent Literatures 38 and 39), and adult T-cell leukemia (Non Patent Literature 40). Moreover, since TfR is expressed on the surface of various types of cancer cells at a high level and is expressed in normal cells at a low level, this receptor had been recognized as a molecular target for cancer therapy from long ago (Non Patent Literatures 13 to 16, and Patent Literatures 1 and 2). However, previously developed anti-human TfR antibodies were all derived from animals. It has been generally known that when an antibody derived from an animal other than a human, such as a mouse antibody, is administered to a human, the administered antibody is recognized as a foreign matter, so that a human antibody against the mouse antibody (Human Anti Mouse Antibody: hereinafter referred to as HAMA) is induced in the human body. It has been known that the HAMA reacts with the administered mouse antibody, and causes side effects (Non Patent Literatures 17 to 20) or accelerates the disappearance of the administered mouse antibody from the body (Non Patent Literatures 18, 21 and 22), thereby reducing the therapeutic effects of the mouse antibody (Non Patent Literatures 23 and 24). In fact, a phase 1 clinical testing was carried out using a certain mouse anti-human TfR antibody. As a result, generation of HAMA was observed, and significant therapeutic effects were not found (Non Patent Literature 25).

In order to avoid such a problem, a chimeric antibody was developed (Patent Literatures 3 and 4). The chimeric antibody comprises portions of two or more species-derived antibodies (a mouse antibody variable region and a human antibody constant region, etc.). Such a chimeric antibody is advantageous in that while it retains the characteristics of a mouse antibody, it has human Fc and thus it is able to stimulate a human complement or cytotoxicity. However, such a chimeric antibody still provokes a "human anti-chimeric antibody," namely HACA (Human Anti-Chimera Antibody) response (Non Patent Literature 26). Moreover, a recombinant antibody, in which only a portion of a substituted antibody is a complementarity determining region (that is, "CDR") was developed (Patent Literatures 5 and 6). Using a CDR transplantation technique, an antibody consisting of a mouse CDR, and human variable region framework and constant region, namely, "humanized antibody" was produced (Non Patent Literature 27). However, even such a humanized antibody has immunogenicity to humans, and thus, causes a HAHA (Human Anti-Human Antibody) reaction (Non Patent Literatures 28 and 29). Accordingly, it has been desired to develop a more safe and effective antibody therapeutic drug having no immunogenicity, which can be applied to clinical sites.

By the way, it is considered essential for development of antibody drugs to obtain an antibody that recognizes a target cancer antigen "in an intact state" that is present on the surface of a cell membrane. However, it has been difficult to obtain even antibodies against known cancer antigens because the target cancer antigens are membrane proteins. In order to overcome such a problem, the present inventors had produced so far an enormous human antibody library consisting of a hundred billion independent clones, and had established a comprehensive method for obtaining antibodies against proteins existing on the cell membrane surface of cancer cells or tissues (cell surface antigens), utilizing the aforementioned library (Patent Literatures 7 to 9).

PRIOR ART LITERATURES

Patent Literatures

Patent Literature 1: U.S. Pat. No. 5,667,781
Patent Literature 2: U.S. Pat. No. 7,976,841
Patent Literature 3: European Patent No. 120694
Patent Literature 4: European Patent No. 125023
Patent Literature 5: U. K. Patent No. GB2188638A
Patent Literature 6: U.S. Pat. No. 5,585,089
Patent Literature 7: International Publication WO01/062907
Patent Literature 8: International Publication WO2001/096401
Patent Literature 9: JP Patent Publication (Kokai) No. 2005-185281

Non Patent Literatures

Non Patent Literature 1: Mass R, et al., Proc Am Soci Clin Oncol 19, 75a, 2000
Non Patent Literature 2: Berinstein N L, et al., Annals of Oncology 1998, 9: 995-1001.
Non Patent Literature 3: Bruggemann M., et al., J. Exp. Med., 166, 1351-1361.
Non Patent Literature 4: Loos M. (1982). Prog. Allergy, 30, 135-192. Mol Immunol. May; 19(5): 651-7.
Non Patent Literature 5: J Clin Invest 1963; 42, 314-326
Non Patent Literature 6: Int J Cancer 1981; 27: 329-334
Non Patent Literature 7: J Urol 1990; 143: 381-385
Non Patent Literature 8: Cancer Gene Ther 2000; 7: 59-65
Non Patent Literature 9: Eur J Cancer 2004; 40 (9): 1418-1422
Non Patent Literature 10: J Clin Invest 1980; 65: 1182-1191.
Non Patent Literature 11: Placenta 1986; 7: 391-403
Non Patent Literature 12: J Clin Invest (1980) 66, 1135-1143. 10
Non Patent Literature 13: Proc. Natl. Acad Sci USA 1982; 79: 1175-1179
Non Patent Literature 14: Cancer Res 1986; 46: 1759-1763
Non Patent Literature 15: Cancer Res 1990; 50: 6295-6301
Non Patent Literature 16: Blood 2004; 103: 1838-1845
Non Patent Literature 17: J. Clin. Oncol., 2, 881 (1984)
Non Patent Literature 18: Blood, 65, 1349 (1985)
Non Patent Literature 19: J. Natl. Cancer Inst., 80, 932 (1988)
Non Patent Literature 20: Proc. Natl. Acad. Sci., U.S.A., 82, 1242 (1985)
Non Patent Literature 21: J. Nucl. Med., 26, 1011 (1985)
Non Patent Literature 22: J. Natl. Cancer Inst., 80, 937 (1988)
Non Patent Literature 23: J. Immunol., 135, 1530 (1985)
Non Patent Literature 24: Cancer Res., 46, 6489 (1986)
Non Patent Literature 25: Clini. Cancer. Res. 1995; 1: 1259-1265
Non Patent Literature 26: J. Exp. Med., 170, 2153-2157, 1989
Non Patent Literature 27: Nature, 332, 323-327, 1988
Non Patent Literature 28: Cancer Res. 2001; 61: 6851-6859,
Non Patent Literature 29: J Pharm Biomed Anal. 2006; 41: 1347-1353
Non Patent Literature 30: Int J Oncol. 1998, 13(4): 871-5
Non Patent Literature 31: Tohoku J. exp. Med. 1987; 153: 239-243
Non Patent Literature 32: Urol. Res. 1987; 15: 341-344
Non Patent Literature 33: Br. J. Urol. 1990; 65: 339-344
Non Patent Literature 34: Histopathology 1988; 12: 53-63
Non Patent Literature 35: J. Clin. Pathol. 1984; 37: 131-135
Non Patent Literature 36: A Pathol. Anat. Histopathol. 1990; 416: 491-496
Non Patent Literature 37: Leukemia 1993; 7: 2019-2025
Non Patent Literature 38: Hematol. Pathol. 1990; 4: 37-41
Non Patent Literature 39: Lancet 1983; 1: 498-501
Non Patent Literature 40: Blood 2004; 103: 1838-1845

SUMMARY OF INVENTION

Problem to be Solved by the Invention

It is a problem to be solved by the present invention to provide a complete human anti-human TfR antibody, which specifically recognizes human TfR, inhibits the survival or growth of cancer cells that highly express TfR, and has no immunogenicity to humans. It is another object of the present invention to provide a method for producing the aforementioned antibody, and a therapeutic agent comprising the aforementioned antibody that is used for disease such as cancer.

Means for Solving the Problem

As mentioned above, an antibody that targets TfR had been developed as an antitumor agent. However, since this antibody had been derived from an animal, the development of an antibody therapeutic drug had not been successful due to generation of HAMA, insufficient drug effects, etc. Thus, the present inventors have conducted intensive studies regarding an original method for antibody production, and as a result, they have obtained a phage antibody (scFv antibody) reacting with TfR existing on the cancer cell membrane, using human antibody library phage display. The inventors have analyzed the sequence of such antibody genes, and as a result, they have found that the CDR of the antibody has a novel amino acid sequence. Furthermore, the inventors have modified such scFv antibodies to provide IgG, so as to produce complete human IgG antibodies. Then, they have examined the antitumor effects of these IgG antibodies in vitro and in vivo. As a result, it was found that the antibodies have strong antitumor effects. As stated above, the present inventors have demonstrated the effectiveness of these antibodies for the treatment of various types of cancers which highly express TfR, thereby completing the present invention.

The present invention provides an antibody which specifically reacts with human TfR, wherein the antibody comprises any one of the amino acid sequences shown in SEQ ID NOS: 1-3, 7-9, 13-15, 19-21, 25-27, 31-33, 37-39, 43-45, 49-51, 55-57, 61-63, 67-69, 73-75, 79-81, 85-87, 91-93, 97-99, 103-105, 109-111, and 115-117, as each of a heavy chain first complementarity determining region (VH CDR1), a heavy chain second complementarity determining region (VH CDR2), and a heavy chain third complementarity determining region (VH CDR3).

The present invention further provides an antibody which specifically reacts with human TfR, wherein the antibody comprises any one of the amino acid sequences shown in SEQ ID NOS: 1-3, 7-9, 13-15, 19-21, 25-27, 31-33, 37-39, 43-45, 49-51, 55-57, 61-63, 67-69, 73-75, 79-81, 85-87, 91-93, 97-99, 103-105, 109-111, and 115-117, as each of a heavy chain first complementarity determining region (VH CDR1), a heavy chain second complementarity determining region (VH CDR2), and a heavy chain third complementarity determining region (VH CDR3), and also comprises any one of the amino acid sequences shown in SEQ ID NOS: 4-6, 10-12, 16-18, 22-24, 28-30, 34-36, 40-42, 46-48, 52-54, 58-60, 64-66, 70-72, 76-78, 82-84, 88-90, 94-96, 100-102, 106-108, 112-114, and 118-120, as each of a light chain first complementarity determining region (VL CDR1), a light chain second complementarity determining region (VL CDR2), and a light chain third complementarity determining region (VL CDR3).

The present invention further provides an antibody which specifically reacts with human TfR and is selected from the following (1) to (20):

(1) an antibody which comprises a heavy chain variable region having CDR consisting of the heavy chain first complementarity determining region (VH CDR1) of SEQ ID NO: 1, the heavy chain second complementarity determining region (VH CDR2) of SEQ ID NO: 2, and the heavy chain third complementarity determining region (VH CDR3) of SEQ ID NO: 3, or CDR substantially identical thereto, and a light chain variable region having CDR consisting of the light chain first complementarity determining region (VL CDR1) of SEQ ID NO: 4, the light chain second complementarity determining region (VL CDR2) of SEQ ID NO: 5, and the light chain third complementarity determining region (VL CDR3) of SEQ ID NO: 6, or CDR substantially identical thereto;

(2) an antibody which comprises a heavy chain variable region having CDR consisting of the heavy chain first complementarity determining region (VH CDR1) of SEQ ID NO: 7, the heavy chain second complementarity determining region (VH CDR2) of SEQ ID NO: 8, and the heavy chain third complementarity determining region (VH CDR3) of SEQ ID NO: 9, or CDR substantially identical thereto, and a light chain variable region having CDR consisting of the light chain first complementarity determining region (VL CDR1) of SEQ ID NO: 10, the light chain second complementarity determining region (VL CDR2) of SEQ ID NO: 11, and the light chain third complementarity determining region (VL CDR3) of SEQ ID NO: 12, or CDR substantially identical thereto;

(3) an antibody which comprises a heavy chain variable region having CDR consisting of the heavy chain first complementarity determining region (VH CDR1) of SEQ ID NO: 13, the heavy chain second complementarity determining region (VH CDR2) of SEQ ID NO: 14, and the heavy chain third complementarity determining region (VH CDR3) of SEQ ID NO: 15, or CDR substantially identical thereto, and a light chain variable region having CDR consisting of the light chain first complementarity determining region (VL CDR1) of SEQ ID NO: 16, the light chain second complementarity determining region (VL CDR2) of SEQ ID NO: 17, and the light chain third complementarity determining region (VL CDR3) of SEQ ID NO: 18, or CDR substantially identical thereto;

(4) an antibody which comprises a heavy chain variable region having CDR consisting of the heavy chain first complementarity determining region (VH CDR1) of SEQ ID NO: 19, the heavy chain second complementarity determining region (VH CDR2) of SEQ ID NO: 20, and the heavy chain third complementarity determining region (VH CDR3) of SEQ ID NO: 21, or CDR substantially identical thereto, and a light chain variable region having CDR consisting of the light chain first complementarity determining region (VL CDR1) of SEQ ID NO: 22, the light chain second complementarity determining region (VL CDR2) of SEQ ID NO: 23, and the light chain third complementarity determining region (VL CDR3) of SEQ ID NO: 24, or CDR substantially identical thereto;

(5) an antibody which comprises a heavy chain variable region having CDR consisting of the heavy chain first complementarity determining region (VH CDR1) of SEQ ID NO: 25, the heavy chain second complementarity determining region (VH CDR2) of SEQ ID NO: 26, and the heavy chain third complementarity determining region (VH CDR3) of SEQ ID NO: 27, or CDR substantially identical thereto, and a light chain variable region having CDR consisting of the light chain first complementarity determining region (VL CDR1) of SEQ ID NO: 28, the light chain second complementarity determining region (VL CDR2) of SEQ ID NO: 29, and the light chain third complementarity determining region (VL CDR3) of SEQ ID NO: 30, or CDR substantially identical thereto;

(6) an antibody which comprises a heavy chain variable region having CDR consisting of the heavy chain first complementarity determining region (VH CDR1) of SEQ ID NO: 31, the heavy chain second complementarity determining region (VH CDR2) of SEQ ID NO: 32, and the heavy chain third complementarity determining region (VH CDR3) of SEQ ID NO: 33, or CDR substantially identical thereto, and a light chain variable region having CDR consisting of the light chain first complementarity determining region (VL CDR1) of SEQ ID NO: 34, the light chain second complementarity determining region (VL CDR2) of SEQ ID NO: 35, and the light chain third complementarity determining region (VL CDR3) of SEQ ID NO: 36, or CDR substantially identical thereto;

(7) an antibody which comprises a heavy chain variable region having CDR consisting of the heavy chain first complementarity determining region (VH CDR1) of SEQ ID NO: 37, the heavy chain second complementarity determining region (VH CDR2) of SEQ ID NO: 38, and the heavy chain third complementarity determining region (VH CDR3) of SEQ ID NO: 39, or CDR substantially identical thereto, and a light chain variable region having CDR consisting of the light chain first complementarity determining region (VL CDR1) of SEQ ID NO: 40, the light chain second complementarity determining region (VL CDR2) of SEQ ID NO: 41, and the light chain third complementarity determining region (VL CDR3) of SEQ ID NO: 42, or CDR substantially identical thereto;

(8) an antibody which comprises a heavy chain variable region having CDR consisting of the heavy chain first complementarity determining region (VH CDR1) of SEQ ID NO: 43, the heavy chain second complementarity determining region (VH CDR2) of SEQ ID NO: 44, and the heavy chain third complementarity determining region (VH CDR3) of SEQ ID NO: 45, or CDR substantially identical thereto, and a light chain variable region having CDR consisting of the light chain first complementarity determining region (VL CDR1) of SEQ ID NO: 46, the light chain second complementarity determining region (VL CDR2) of SEQ ID NO: 47, and the light chain third complementarity determining region (VL CDR3) of SEQ ID NO: 48, or CDR substantially identical thereto;

(9) an antibody which comprises a heavy chain variable region having CDR consisting of the heavy chain first complementarity determining region (VH CDR1) of SEQ ID NO: 49, the heavy chain second complementarity determining region (VH CDR2) of SEQ ID NO: 50, and the heavy chain third complementarity determining region (VH CDR3) of SEQ ID NO: 51, or CDR substantially identical thereto, and a light chain variable region having CDR consisting of the light chain first complementarity determining region (VL CDR1) of SEQ ID NO: 52, the light chain second complementarity determining region (VL CDR2) of SEQ ID NO: 53, and the light chain third complementarity determining region (VL CDR3) of SEQ ID NO: 54, or CDR substantially identical thereto;

(10) an antibody which comprises a heavy chain variable region having CDR consisting of the heavy chain first complementarity determining region (VH CDR1) of SEQ ID NO: 55, the heavy chain second complementarity determining region (VH CDR2) of SEQ ID NO: 56, and the heavy chain third complementarity determining region (VH CDR3) of SEQ ID NO: 57, or CDR substantially identical thereto, and a light chain variable region having CDR consisting of the light chain first complementarity determining region (VL CDR1) of SEQ ID NO: 58, the light chain second complementarity determining region (VL CDR2) of SEQ ID NO: 59, and the light chain third complementarity determining region (VL CDR3) of SEQ ID NO: 60, or CDR substantially identical thereto;

(11) an antibody which comprises a heavy chain variable region having CDR consisting of the heavy chain first complementarity determining region (VH CDR1) of SEQ ID NO: 61, the heavy chain second complementarity determining region (VH CDR2) of SEQ ID NO: 62, and the heavy chain third complementarity determining region (VH CDR3) of SEQ ID NO: 63, or CDR substantially identical thereto, and a light chain variable region having CDR consisting of the light chain first complementarity determining region (VL CDR1) of SEQ ID NO: 64, the light chain second complementarity determining region (VL CDR2) of SEQ ID NO: 65, and the light chain third complementarity determining region (VL CDR3) of SEQ ID NO: 66, or CDR substantially identical thereto;

(12) an antibody which comprises a heavy chain variable region having CDR consisting of the heavy chain first complementarity determining region (VH CDR1) of SEQ ID NO: 67, the heavy chain second complementarity determining region (VH CDR2) of SEQ ID NO: 68, and the heavy chain third complementarity determining region (VH CDR3) of SEQ ID NO: 69, or CDR substantially identical thereto, and a light chain variable region having CDR consisting of the light chain first complementarity determining region (VL CDR1) of SEQ ID NO: 70, the light chain second complementarity determining region (VL CDR2) of SEQ ID NO: 71, and the light chain third complementarity determining region (VL CDR3) of SEQ ID NO: 72, or CDR substantially identical thereto;

(13) an antibody which comprises a heavy chain variable region having CDR consisting of the heavy chain first complementarity determining region (VH CDR1) of SEQ ID NO: 73, the heavy chain second complementarity determining region (VH CDR2) of SEQ ID NO: 74, and the heavy chain third complementarity determining region (VH CDR3) of SEQ ID NO: 75, or CDR substantially identical thereto, and a light chain variable region having CDR consisting of the light chain first complementarity determining region (VL CDR1) of SEQ ID NO: 76, the light chain second complementarity determining region (VL CDR2) of SEQ ID NO: 77, and the light chain third complementarity determining region (VL CDR3) of SEQ ID NO: 78, or CDR substantially identical thereto;

(14) an antibody which comprises a heavy chain variable region having CDR consisting of the heavy chain first complementarity determining region (VH CDR1) of SEQ ID NO: 79, the heavy chain second complementarity determining region (VH CDR2) of SEQ ID NO: 80, and the heavy chain third complementarity determining region (VH CDR3) of SEQ ID NO: 81, or CDR substantially identical thereto, and a light chain variable region having CDR consisting of the light chain first complementarity determining region (VL CDR1) of SEQ ID NO: 82, the light chain second complementarity determining region (VL CDR2) of SEQ ID NO: 83, and the light chain third complementarity determining region (VL CDR3) of SEQ ID NO: 84, or CDR substantially identical thereto;

(15) an antibody which comprises a heavy chain variable region having CDR consisting of the heavy chain first complementarity determining region (VH CDR1) of SEQ ID NO: 85, the heavy chain second complementarity determining region (VH CDR2) of SEQ ID NO: 86, and the heavy chain third complementarity determining region (VH CDR3) of SEQ ID NO: 87, or CDR substantially identical thereto, and a light chain variable region having CDR consisting of the light chain first complementarity determining region (VL CDR1) of SEQ ID NO: 88, the light chain second complementarity determining region (VL CDR2) of SEQ ID NO: 89, and the light chain third complementarity determining region (VL CDR3) of SEQ ID NO: 90, or CDR substantially identical thereto;

(16) an antibody which comprises a heavy chain variable region having CDR consisting of the heavy chain first complementarity determining region (VH CDR1) of SEQ ID NO: 91, the heavy chain second complementarity determining region (VH CDR2) of SEQ ID NO: 92, and the heavy chain third complementarity determining region (VH CDR3) of SEQ ID NO: 93, or CDR substantially identical thereto, and a light chain variable region having CDR consisting of the light chain first complementarity determining region (VL CDR1) of SEQ ID NO: 94, the light chain second complementarity determining region (VL CDR2) of SEQ ID NO: 95, and the light chain third complementarity determining region (VL CDR3) of SEQ ID NO: 96, or CDR substantially identical thereto;

(17) an antibody which comprises a heavy chain variable region having CDR consisting of the heavy chain first complementarity determining region (VH CDR1) of SEQ ID NO: 97, the heavy chain second complementarity determining region (VH CDR2) of SEQ ID NO: 98, and the heavy chain third complementarity determining region (VH CDR3) of SEQ ID NO: 99, or CDR substantially identical thereto, and a light chain variable region having CDR consisting of the light chain first complementarity determining region (VL CDR1) of SEQ ID NO: 100, the light chain second complementarity determining region (VL CDR2) of SEQ ID NO: 101, and the light chain third complementarity determining region (VL CDR3) of SEQ ID NO: 102, or CDR substantially identical thereto;

(18) an antibody which comprises a heavy chain variable region having CDR consisting of the heavy chain first complementarity determining region (VH CDR1) of SEQ ID NO: 103, the heavy chain second complementarity determining region (VH CDR2) of SEQ ID NO: 104, and the heavy chain third complementarity determining region (VH CDR3) of SEQ ID NO: 105, or CDR substantially identical thereto, and a light chain variable region having CDR consisting of the light chain first complementarity determining region (VL CDR1) of SEQ ID NO: 106, the light chain second complementarity determining region (VL CDR2) of SEQ ID NO: 107, and the light chain third complementarity determining region (VL CDR3) of SEQ ID NO: 108, or CDR substantially identical thereto;

(19) an antibody which comprises a heavy chain variable region having CDR consisting of the heavy chain first complementarity determining region (VH CDR1) of SEQ ID NO: 109, the heavy chain second complementarity determining region (VH CDR2) of SEQ ID NO: 110, and the heavy chain third complementarity determining region (VH CDR3) of SEQ ID NO: 111, or CDR substantially identical thereto, and a light chain variable region having CDR consisting of the light chain first complementarity determining region (VL CDR1) of SEQ ID NO: 112, the light chain second complementarity determining region (VL CDR2) of SEQ ID NO: 113, and the light chain third complementarity determining region (VL CDR3) of SEQ ID NO: 114, or CDR substantially identical thereto; and

(20) an antibody which comprises a heavy chain variable region having CDR consisting of the heavy chain first complementarity determining region (VH CDR1) of SEQ ID NO: 115, the heavy chain second complementarity determining region (VH CDR2) of SEQ ID NO: 116, and the heavy chain third complementarity determining region (VH CDR3) of SEQ ID NO: 117, or CDR substantially identical thereto, and a light chain variable region having CDR consisting of the light chain first complementarity determining region (VL CDR1) of SEQ ID NO: 118, the light chain second complementarity determining region (VL CDR2) of SEQ ID NO: 119, and the light chain third complementarity determining region (VL CDR3) of SEQ ID NO: 120, or CDR substantially identical thereto.

The present invention further provides an antibody which specifically reacts with human TfR, and which comprises a deletion, addition, substitution and/or insertion of one or several amino acids with respect to any one of the amino acid sequences shown in SEQ ID NOS: 1-3, 7-9, 13-15, 19-21, 25-27, 31-33, 37-39, 43-45, 49-51, 55-57, 61-63, 67-69, 73-75, 79-81, 85-87, 91-93, 97-99, 103-105, 109-111, 115-117, 4-6, 10-12, 16-18, 22-24, 28-30, 34-36, 40-42, 46-48, 52-54, 58-60, 64-66, 70-72, 76-78, 82-84, 88-90, 94-96, 100-102, 106-108, 112-114, and 118-120, and which has an activity equivalent to the activity of the antibody according to any one of claims 1 to 3.

Preferably, the antibody of the present invention is a human antibody or a humanized antibody.

Preferably, the antibody of the present invention is an antibody fragment selected from the group consisting of Fab, Fab', F(ab')$_2$, a single-chain antibody (scFv), a dimerized V region (Diabody), a disulfide-stabilized V region (dsFv) and a peptide comprising CDR.

The present invention provides DNA which encodes the antibody of the present invention as mentioned above.

The present invention provides a recombinant vector which comprises the DNA of the present invention as mentioned above.

The present invention provides a transformed cell line which is obtained by introducing the recombinant vector of the present invention as mentioned above into a host cell.

The present invention provides a method for producing the antibody of the present invention, which comprises culturing the transformed cell line of the present invention as mentioned above in a medium, generating and accumulating the antibody of the present invention in the culture, and then collecting the antibody from the culture.

The present invention provides a pharmaceutical composition which comprises the antibody of the present invention as mentioned above.

The present invention provides the pharmaceutical composition as mentioned above, wherein a cytotoxic substance is bound to the antibody.

Preferably, the cytotoxic substance is a drug, a toxin, or a radioactive substance.

Preferably, the pharmaceutical composition of the present invention is used as an anticancer agent.

Preferably, the cancer is a solid cancer or a blood cancer.

Preferably, the solid cancer is lung cancer, colon cancer, stomach cancer, bladder cancer, pancreatic cancer, prostate cancer, hepatic cancer, cervical cancer, uterine cancer, ovarian cancer, breast cancer, head and neck cancer, or skin cancer.

Preferably, the blood cancer is leukemia, lymphoma, or myeloma.

Further preferably, the blood cancer is adult T-cell leukemia (ATL).

The present invention further provides a method for suppressing or treating a cancer which comprises administering the antibody of the present invention as mentioned above to a subject.

The present invention further provides a use of the antibody of the present invention as mentioned above for production of a pharmaceutical composition or an anticancer agent.

Advantageous Effects of Invention

The antibody of the present invention is a complete human antibody, which specifically recognizes human TfR and inhibits the survival or growth of cancer cells that express TfR. When a human antibody is administered to a human, the antigenicity of the antibody is significantly reduced, and HAHA is not thereby generated. Hence, the human antibody can exhibit high antitumor action, causing a few side effects. That is to say, the anti-human TfR antibody of the present invention is useful as an anticancer agent.

DESCRIPTION OF EMBODIMENTS

Figure 1:
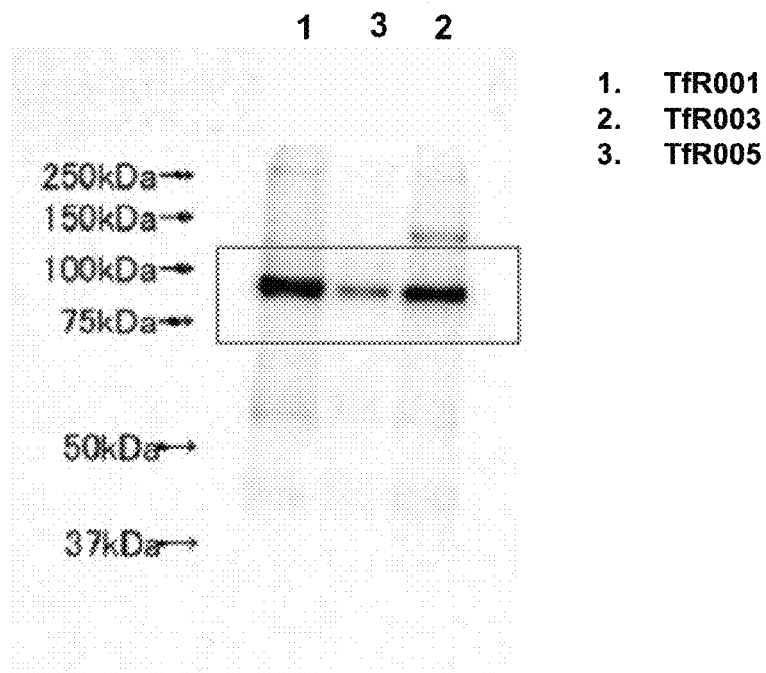
FIG. 1 shows the results obtained by confirming the TfR-binding ability of anti-TfR phage antibodies by immunoprecipitation and Western blotting.

Hereinafter, the present invention will be described more in detail.

Definitions and General Techniques

Unless otherwise specified in the present description, scientific terms used regarding the present invention have meanings that are generally understood by a person skilled in the art. In general, nomenclatures and techniques applied to the cell and tissue culture, molecular biology, immunology, microbiology, genetics, protein and nucleic acid chemistry, and hybridization, which are described in the present description, are well known in the present technical field, and thus, are commonly used.

The methods and techniques of the present invention are carried out in accordance with conventional methods that are well known in the present technical field, in such ways as described in a variety of general reference documents cited and discussed throughout the present description and more specific reference documents, unless otherwise specified.
TfR Human transferrin receptor (TfR) is a single-pass transmembrane protein (SEQ ID NO: 125) comprising 760 amino acids, and it is encoded by human chromosome 3. This protein has also been known as a CD71 antigen, and it is considered that this protein is associated with incorporation of iron into cells and cell growth. The TfR of the present invention is not particularly limited in terms of structure. Thus, human TfR includes all of a monomer, a multimer, an intact form expressed on a cell membrane, a soluble form constituted in an extracellular region, a truncated form, a mutation form caused by genetic mutation, deletion, etc., and a form that has undergone posttranslational modification by phosphorylation or the like.
React and Reactivity The terms "react" and "reactivity" have the same meanings in the present description, unless otherwise specified. That is, these terms mean that an antibody recognizes an antigen. The antigen used herein may be any of an intact TfR expressed on a cell membrane, a truncated form, and a soluble form. In addition, the antigen may be either a TfR having a three-dimensional structure or a denatured TfR. Examples of a means for examining reactivity include flow cytometry (FACS), enzyme-linked immunosorbent assay (ELISA), Western blotting, Fluorometric Microvolume Assay Technology (FMAT), surface plasmon resonance (Biacore), immunostaining, and immunoprecipitation.

The antibody used in flow cytometry may be either an antibody labeled with a fluorescent substance such as FITC or with biotin, or an unlabeled antibody. A fluorescently-labeled avidin, a fluorescently-labeled anti-human immunoglobulin antibody, or the like is used, depending on the presence or absence of labeling of the antibody used and the type thereof. Reactivity can be evaluated by adding a sufficient amount of anti-TfR antibody (generally having a final concentration of 0.01 to 10 µg/mL) to an analyte, and then by comparing the obtained reactivity with the reactivity with a negative control antibody or a positive control antibody.
Antibody In the present description, the following abbreviations (in the parentheses) are used in accordance with the customs, as necessary.

Heavy chain (H chain), light chain (L chain), heavy chain variable region (VH), light chain variable region (VL), complementarity determining region (CDR), first complementarity determining region (CDR1), second complementarity determining region (CDR2), third complementarity determining region (CDR3), heavy chain first complementarity determining region (VH CDR1), heavy chain second complementarity determining region (VH CDR2), heavy chain third complementarity determining region (VH CDR3), light chain first complementarity determining region (VL CDR1), light chain second complementarity determining region (VL CDR2), and light chain third complementarity determining region (VL CDR3).

In the present description, the term "antibody" has the same definitions as immunoglobulin, and should be understood as generally known in the present technical field. Specifically, the term "antibody" is not limited by any given specific method for producing the antibody. For example, the term "antibody" includes, but is not limited to, a recombinant antibody, a monoclonal antibody, and a polyclonal antibody.

In the present description, the term "human antibody is used to mean any given antibody, in which the sequences of a variable region and a constant region are human sequences. This term includes antibodies which have human sequences and are modified, for example, to remove cysteine that may cause a possible decrease in immunogenicity, an increase in affinity, and undesirable folding. This term also includes antibodies produced in non-human cells by recombination, which enable glycosylation that is not specific to human cells. These antibodies can be prepared in various ways.

In the present description, the term "humanized antibody" means a non-human-derived antibody, in which amino acid residues characteristic for a non-human antibody sequence are substituted with residues found in positions corresponding to those of a human antibody. This "humanization" process is considered to reduce the immunogenicity of the obtained antibody in human. It would be understood that a non-human-derived antibody can be humanized using a technique well known in the present technical field. Please refer to, for example, Winter et al., Immunol. Today 14: 43-46 (1993). The antibody of interest can be produced by an engineering approach via a recombination DNA technique of substituting CH1, CH2, CH3, a hinge domain, and/or a framework domain with those of the corresponding human sequence. For example, WO92/02190, and U.S. Pat. Nos. 5,530,101, 5,585,089, 5,693,761, 5,693,792, 5,714,350 and 5,777,085 can be referred to. In the present description, the term "humanized antibody" includes a chimeric human antibody and a CDR-grafted antibody, within the definitions thereof.

The sequence of a framework region (FR) in a variable region of the antibody of the present invention is not particularly limited, unless it substantially affects the specific binding ability of the antibody to the corresponding antigen. The FR region of a human antibody is preferably used, but it is also possible to use FR regions of animal species other than humans (e.g. a mouse, a rat, etc.).

In the present description, the term "phage antibody" is used to mean a scFv antibody generated from phage. That is, the phage antibody is an antibody fragment comprising the amino acid sequence of VH and VL. This fragment may comprise an amino acid sequence serving as a tag, as well as amino acids serving as a linker.

In one aspect, the antibody of the present invention comprises a constant region as well as a variable region (e.g. IgG antibody). The sequence of such a constant region is not particularly limited. For example, the constant region of a known human antibody can be used. The heavy chain constant region (CH) of a human antibody is not particularly limited, as long as it belongs to a human immunoglobulin (hereinafter referred to as "hIg"). Those of hIgG class are preferable, and any one of subclasses belonging to hIgG class, such as hIgG1, hIgG2, hIgG3 or hIgG4, may be used. On the other hand, the light chain constant region (CL) of a human antibody is not particularly limited, as long as it belongs to hIg, and those of κ class or λ class can be used. In addition, constant regions of animal species other than humans (e.g. a mouse or a rat) can also be used.

With regard to the amino acid sequence of FR or constant region used in the antibody of the present invention, the amino acid sequence of the original FR or constant region may be directly used. Otherwise, a different amino acid sequence may be prepared by deleting, adding, substituting and/or inserting one or several (for example, 1 to 8, preferably 1 to 5, more preferably 1 to 3, and particularly preferably 1 or 2) amino acids, with respect to the original amino acid sequence, and it may be then used.

In the present invention, the phrase "an activity equivalent to the activity of the antibody according to the claims" is used to mean that the binding activity and/or antitumor activity of a certain antibody to human TfR is equivalent to that of the antibody according to the claims. The term "binding activity" means that the activity of an antibody to recognize an antigen. This antigen may be an intact TfR expressed on a cell membrane, a truncated form, or a soluble form. In addition, the antigen may be either a TfR having a three-dimensional structure or a denatured TfR. Examples of a means for examining the binding activity include flow cytometry (FACS), enzyme-linked immunosorbent assay (ELISA), Western blotting, Fluorometric Microvolume Assay Technology (FMAT), and surface plasmon resonance (Biacore). The term "antitumor activity" means the activity of inhibiting the growth or survival of tumor cells. The inhibition of the growth or survival of tumor cells may take place either in vitro or in vivo. Examples of the in vitro antitumor activity include an activity of decreasing the number of tumor cells, an activity of inhibiting an increase in the number of tumor cells, an activity of causing cell death to tumor cells, antibody-dependent cellular cytotoxicity (ADCC), and complement-dependent cytotoxicity (CDC). Examples of the in vivo antitumor activity include an activity of decreasing the weight or volume of a tumor, an activity of suppressing an increase in tumor weight or volume, an activity of promoting a decrease in tumor weight or volume by other agents, and an activity of suppressing the death of individuals caused by tumor cells.

Examples of an in vivo animal model include: a xenograft model prepared by transplanting a human cancer tissue-derived cultured cell line into an immunodeficient mouse such as a nude mouse; and a syngeneic graft model prepared by transplanting a cultured mouse cancer cell line into a wild-type mouse having a normal immune system.

A xenograft model can be produced by transplanting a human cancer cell line into various sites of immunodeficient mice such as a nude mouse, including the subcutis, intradermal site, abdominal cavity, or vein.

In the present invention, the term "equivalent" does not necessarily mean the same level of activity. The activity may be increased, or it may be decreased as long as there is an activity. An antibody having a decreased activity may be an antibody having an activity of, for example, 30% or more, preferably 50% or more, more preferably 80% or more, further preferably 90% or more, and particularly preferably 95% or more, when compared with the original antibody.

The aforementioned antibody may comprise a substitution, deletion, addition and/or insertion of one or multiple amino acids with respect to the amino acid sequence of a variable region (a CDR sequence and/or an FR sequence), as far as it has a binding activity to TfR or an antitumor activity that is equivalent to that of the original antibody. As a method for preparing an antibody having a TfR-binding activity and/or an antitumor activity, which comprises a deletion, addition, substitution and/or insertion of one or several amino acids (for example, 1 to 8, preferably 1 to 5, more preferably 1 to 3, and particularly preferably 1 or 2 amino acids), a method of introducing a mutation into a protein has been well known to a person skilled in the art. For instance, such a skilled person could prepare a mutant antibody functionally equivalent to an antibody having a TfR-binding activity and/or an antitumor activity by appropriately introducing a mutation into the amino acid sequence of the antibody having a TfR-binding activity and/or an antitumor activity according to a site-directed mutagenesis (Hashimoto-Gotoh, T, Mizuno, T, Ogasahara, Y, an DNA kagawa, M. (1995) An oligodeoxyribonucleotide-directed dual amber method for site-directed mutagenesis. Gene 152, 271-275, Zoller, M J, and Smith, M. (1983) Oligonucleotide-directed mutagenesis of DNA fragments cloned into M13 vectors. Methods Enzymol. 100, 468-500, Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456, Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492), etc.

As such, an antibody, which comprises a mutation of one or several amino acids in a variable region thereof and has a TfR-binding activity and/or an antitumor activity, is also included in the antibody of the present invention.

In the present description, the phrase "CDR substantially identical thereto" is used to mean CDR that constitutes the aforementioned antibody comprising a deletion, addition, substitution and/or insertion of one or several amino acids and having a TfR-binding activity and/or an antitumor activity.

The antibody of the present invention is not limited by its origin, and it may be an antibody derived from any animal, such as a human antibody, a mouse antibody, or a rat antibody. Also, the present antibody may be a chimeric antibody or a humanized antibody. In a preferred aspect, the antibody of the present invention is a human antibody.

The antibodies of the present invention may be different from one another in terms of amino acid sequence, molecular weight, isoelectric point, the presence or absence of a sugar chain or the form thereof, etc., depending on the after-mentioned cells or hosts that produce the antibodies, or a purification method. As long as the obtained antibody has an activity equivalent to the activity of the antibody of the present invention, it is included in the present invention. For example, an antibody that undergoes a modification after it has been translated to the amino acid sequence described in the present description is also included in the present invention. Moreover, an antibody that has undergone a posttranslational modification on a site other than those for the known posttranslational modification is also included in the present invention, as long as it has an activity equivalent to the activity of the antibody of the present invention. Furthermore, when the antibody of the present invention is allowed to express in prokaryotic cells such as *Escherichia coli*, a methionine residue is added to the N-terminus of the amino acid sequence of the original antibody. The antibody of the present invention includes such an antibody as well. An antibody that has undergone a posttranslational modification on a site other than those for the known posttranslational modification is also included in the present invention, as long as it has an activity equivalent to the antibody of the present invention.

Production of Antibody (1) scFv Reacting with Antigen Using Phage Display Library The antibody of the present invention can be prepared by several methods known in the present technical field. For example, using a phage display technique, a library comprising a repertoire of antibodies having various affinity for TfR can be provided. Subsequently, such a library can be screened to identify and isolate antibodies against TfR. Preferably, the phage library is a scFv phage display library that is generated using human VL and VH cDNA that has been prepared from mRNA isolated from human B cells. A method of preparing and screening such a library is known in the present technical field. A genetic substance is recovered from phage clones exhibiting reactivity that have been screened using a human TfR as an antigen. By analyzing the selected phage gene, the DNA sequences of VH and VL encoding the variable region of a human antibody binding to the antigen can be determined Using this scFv sequence, IgG is prepared from scFv, so as to obtain a human antibody.

(2) Preparation of IgG from scFv (Preparation of Human Antibody)

An expression vector of H chain or L chain is produced, and it is then allowed to express in a host cell. Thereafter, the secreted supernatant is recovered and is then purified, so as to obtain a human antibody. Alternatively, such a human antibody can also be obtained by allowing VH and VL to express in a single vector (tandem type). These methods are well known, and can be carried out with reference to WO92/01047, WO92/20791, WO93/06213, WO93/11236, WO93/19172, WO95/01438, WO95/15388, WO97/10354, etc.

Specifically, DNA encoding VH is ligated to another DNA molecule encoding a heavy chain constant region (CH1, CH2 and CH3), so as to obtain a full-length heavy chain gene. The sequence of a human heavy chain constant region gene is known in the present technical field (for example, Kabat, E. A. et al., (1991) Sequences of Proteins of Immunological Interest, $5^{th}$ edition, U.S. Department of Health and Human Services, NIH Publication No. 91-3242), and a DNA fragment including such a region can be obtained by standard PCR amplification. The heavy chain constant region may be the constant region of IgG1, IgG2, IgG3, IgG4, IgA, IgE, IgM or IgD. The most preferred constant region is that of IgG1 or IgG2. The constant region sequence of IgG1 may include any given various alleles or allotypes known to be generated among different individuals, such as Gm (1), Gm (2), Gm (3) or Gm (17). These allotypes correspond to a substitution of amino acids naturally-occurring in the constant region of IgG1.

DNA encoding VL is ligated to another DNA molecule encoding the light chain constant region CL, so as to obtain a full-length L chain gene (and a Fab light chain gene). The sequence of a human light chain constant region gene is known in the present technical field (for example, Kabat, E. A. et al., (1991) Sequences of Proteins of Immunological Interest, $5^{th}$ edition, U.S. Department of Health and Human Services, NIH Publication No. 91-3242), and a DNA fragment including such a region can be obtained by standard PCR amplification. The light chain constant region may be the constant region of κ or λ. The K constant region may include any given various alleles known to be generated among different individuals, such as Inv (1), Inv (2) or Inv (3). The λ constant region may be derived from any one of the three λ genes.

The thus obtained DNA encoding an H chain or L chain is inserted into an expression vector to produce an expression vector, and the produced expression vector is then allowed to express in a host cell. Thereafter, the secreted supernatant is recovered and purified to obtain a human antibody. Examples of the expression vector include a plasmid, retrovirus, adenovirus, adeno-associated virus (AAV), plant viruses such as cauliflower mosaic virus or tobacco mosaic virus, a cosmid, YAC, and EBV-derived episome. An expression vector and an expression regulatory sequence are selected, so that they are suitable for a host cell used for expression. An antibody light chain gene and an antibody heavy chain gene can be inserted into different vectors, or the two genes can also be inserted into a single expression vector. An antibody gene is inserted into an expression vector by a standard method (for example, ligation of a complementary restriction site on an antibody gene fragment to a vector, or blunt-ended ligation when no restriction sites are present).

A preferred vector encodes a functionally completed human CH or CL immunoglobulin sequence having a suitable restriction site, which has been produced by an engineering approach such that any given VH or VL sequence can be easily inserted and then expressed therein, as described above. In such a vector, splicing generally takes place between a splice donor site in the inserted J region and a splice acceptor site preceding a human C domain, or such splicing also takes place in a splice region existing in a human CH exon. Polyadenylation and transcription termination take place in a natural chromosomal site downstream of a coding region. A recombinant expression vector can also encode a signal peptide that promotes the secretion of an antibody chain derived from a host cell. An antibody chain gene can be cloned into a vector, such that a signal peptide can be ligated in-frame to the amino terminus of an immunoglobulin chain. The signal peptide may be either an immunoglobulin signal peptide or a heterogeneous signal peptide (namely, it may be a non-immunoglobulin protein-derived signal peptide).

An expression vector for the antibody of the present invention may also have sequences such as a sequence for regulating replication of the vector in a host cell (e.g. a replication origin) or a selective marker gene sequence, as well as an antibody gene and a regulatory sequence. The selective marker gene promotes selection of a host cell into which a vector has been introduced. For instance, the selective marker generally imparts resistance to drugs such as G418, hygromycin or methotrexate to a host cell into which the vector has been introduced. Preferred selective marker genes include a dihydrofolate reductase (DHFR) gene (used with methotrexate selection/amplification in dhfr-host cell), a neomycin phosphotransferase gene (for G418 selection), and a glutamate synthase gene.

A host cell is transformed with an antibody gene expression vector produced by the above described method. Any type of cell may be used as a host cell, as long as it can produce the antibody of the present invention. Examples of such a host cell include bacteria, yeast, animal cells, insect cells, and plant cells. Among these cells, animal cells are preferable. Examples of the animal cells include Chinese hamster ovary cells CHO/dhfr(−) and CHO/DG44, monkey-derived cells COS (A. Wright & S. L. Morrison, J. Immunol. 160, 3393-3402 (1998)), and SP2/O cells (mouse myeloma) (K. Motmans et al., Eur. J. Cancer Prev. 5, 512-5199 (1996), R. P. Junghans et al., Cancer Res. 50, 1495-1502 (1990)). For transformation, a lipofectin method (R. W. Malone et al., Proc. Natl. Acad. Sci. USA 86, 6007 (1989), P. L. Felgner et al., Proc. Natl. Acad. Sci. USA 84, 7413 (1987)), an electroporation method, a calcium phosphate method (F. L. Graham & A. J. van der Eb, Virology 52, 456-467 (1973)), a DEAE-Dextran method, and the like are preferably applied.

A transformant is cultured, and a human antibody is then separated from the cells of the transformant or a culture medium thereof. For separation/purification of the antibody, methods such as centrifugation, ammonium sulfate fractionation, salting-out, ultrafiltration, affinity chromatography, ion exchange chromatography and gel filtration chromatography can be used by appropriately combining them.

Antibody Fragments

An antibody fragment can be produced based on the antibody of the present invention, or based on the sequence information of a gene encoding the antibody of the present invention. Examples of the antibody fragment include Fab, Fab', F(ab')$_2$, scFv, and dsFv antibodies.

Fab is obtained by digesting IgG by papain in the presence of cysteine, and is an antibody fragment with a molecular weight of approximately 50,000, which is constituted with L chain and H chain variable regions, and an H chain fragment consisting of a CH1 domain and a portion of a hinge region. In the present invention, Fab can be obtained by papain digestion of the above-described antibody. In addition, Fab can also be prepared by incorporating DNA encoding a portion of the H chain and the L chain of the above-described antibody into a suitable vector, then performing transformation with the resulting vector, and then obtaining Fab from the transformant.

Fab' is an antibody fragment with a molecular weight of approximately 50,000, which is obtained by cleaving a disulfide bond between the H chains of the below-mentioned F(ab')$_2$. In the present invention, Fab' can be obtained by digesting the above-described antibody by pepsin, and then cleaving a disulfide bond with a reducing agent. In addition, as with Fab, Fab' can also be prepared by genetic engineering using DNA encoding the Fab'.

F(ab')$_2$ is an antibody fragment with a molecular weight of approximately 100,000, which is obtained by binding, via a disulfide bond, one fragment (Fab') constituted with L chain and H chain variable regions and an H chain fragment consisting of a CH1 domain and a portion of a hinge region, to the other fragment (Fab'), wherein Fab' is obtained by digesting IgG by pepsin. In the present invention, F(ab')$_2$ can be obtained by digesting the above-described antibody by pepsin. In addition, as with Fab, F(ab')$_2$ can also be prepared by genetic engineering using DNA encoding the F(ab')$_2$.

scFv is an antibody fragment obtained by ligating the C-terminus of one chain of Fv consisting of an H chain variable region and an L chain variable region to the N-terminus of the other chain thereof using a suitable peptide linker, so as to form a single chain. (GGGGS)$_3$ having high flexibility can be used, for example, as such a peptide linker. For instance, DNA encoding the H chain variable region and L chain variable region of the above-described antibody and DNA encoding a peptide linker are used to construct DNA encoding a scFv antibody, and the thus constructed DNA is then incorporated into a suitable vector. Thereafter, scFv can be prepared from a transformant obtained by transformation with the aforementioned vector.

dsFv is a Fv fragment obtained by introducing a Cys residue into a suitable site in each of an H chain variable region and an L chain variable region, and then stabilizing the H chain variable region and the L chain variable region by a disulfide bond. The site in each chain, into which the Cys residue is to be introduced, can be determined based on a conformation predicted by molecular modeling. In the present invention, for example, a conformation is predicted from the amino acid sequences of the H chain variable region and L chain variable region of the above-described antibody, and DNA encoding each of the H chain variable region and the L chain variable region, into which a mutation has been introduced based on such prediction, is then constructed. The thus constructed DNA is incorporated into a suitable vector. Thereafter, dsFv can be then prepared from a transformant obtained by transformation with the aforementioned vector.

Further, it is also possible to ligate the scFv antibody to the dcFv antibody or the like using a suitable linker, or to fuse an antibody fragment with streptavidin, so as to multimerize the antibody fragment.

Pharmaceutical Composition

According to the present invention, a pharmaceutical composition comprising the antibody of the present invention is provided. In one embodiment, the present invention relates to the treatment of cancer, but is not limited thereto. Diseases caused by high expression of TfR, other than cancer, are also included in the scope of the present invention. In a more preferred embodiment, examples of the cancer include: solid cancer (e.g. lung cancer, colon cancer, stomach cancer, bladder cancer, pancreatic cancer, prostate cancer, hepatic cancer, cervical cancer, uterine cancer, ovarian cancer, breast cancer, head and neck cancer, skin cancer, etc.); and blood cancer (e.g. leukemia, lymphoma, myeloma, etc.). In another preferred embodiment of the present invention, the cancer is adult T-cell leukemia (ATL).

In one aspect of the pharmaceutical composition of the present invention, the antibody of the present invention is used as an active ingredient. The cell growth-suppressing activity, cell death-inducing activity, ADCC activity, CDC activity and the like of the antibody are utilized, and thereby, the antitumor effects of the antibody are exhibited. The antibody may have only one of the aforementioned activities, or may simultaneously have a plurality of the aforementioned activities. That is, a naked antibody is used as an active ingredient of the pharmaceutical composition.

In another aspect, the antibody of the present invention can be used as a cancer therapeutic agent in a missile therapy that specifically targets cancer tissues. Specifically, the missile therapy is a treatment method, which comprises administering to cancer cells, an antibody to which a substance causing damage to the cancer cells has been bound, and allowing the substance to specifically transfer to the cancerous portion, so as to address the achievement of therapeutic effects and reduction in side effects.

The substances causing damage to cancer cells are cytotoxic substances such as a drug, a toxin or a radioactive substance. The binding of such a cytotoxic substance to the antibody can be carried out by a method known to a person skilled in the art (Clin Cancer Res. 2004 Jul. 1; 10(13): 4538-49).

As a drug to be bound to the antibody, a known substance causing damage to cancer cells can be used. Examples of such a drug include duocarmycin, an analog and a derivative of duocarmycin, CC-1065, a duocarmycin analog comprising CBI as a main ingredient, a duocarmycin analog comprising MCBI as a main ingredient, a duocarmycin analog comprising CCBI as a main ingredient, doxorubicin, a doxorubicin conjugate, morpholino-doxorubicin, cyanomorpholino-doxorubicin, dolastatin, dolestatin-10, combretastatin, calicheamicin, maytansine, a maytansine analog, DM1, DM2, DM3, DM4, DMI, auristatin E, auristatin EB (AEB), auristatin EFP (AEFP), monomethyl auristatin E (MMAE), monomethyl auristatin F (MMAF), 5-benzoyl valeric acid-AE ester (AEVB), tubulysin, disorazole, epothilone, paclitaxel, docetaxel, SN-38, topotecan, rhizoxin, echinomycin, colchicine, vinblastine, vindesine, estramustine, cemadotin, eleutherobin, methotrexate, methopterin, dichloromethotrexate, 5-fluorouracil, 6-mercaptopurine, cytosine arabinoside, melphalan, leurosine, leurosideine, actinomycin, daunorubicin, a daunorubicin conjugate, mitomycin C, mitomycin A, caminomycin, aminopterin, talisomycin, podophyllotoxin, a podophyllotoxin derivative, etoposide, etoposide phosphate, vincristine, taxol, taxotere retinoic acid, butyric acid, $N^8$-acetyl spermidine and camptothecin, but examples are not limited thereto.

The antibody may be directly bound to a drug via a linking group possessed thereby or the like, or they may be indirectly bound to each other via a linker or another substance.

Examples of the use of a linking group in the direct binding of a drug include a disulfide bond using an SH group and a bond mediated by maleimide. For example, an intramolecular disulfide bond in the Fc region of the antibody and a disulfide bond of the drug are reduced, and they are then bound to each other via a disulfide bond. There is also a method involving mediation of maleimide. In addition, an alternative method is a method of introducing cysteine into the antibody by genetic engineering.

It is also possible to indirectly bind the antibody to the drug via another substance (linker). The linker desirably has one or two or more types of functional groups reacting with the antibody or the drug, or with both of them. Examples of such a functional group include an amino group, a carboxyl group, a mercapto group, a maleimide group, and a pyridinyl group.

Examples of the linker used herein include N-succinimidyl 4-(maleimidomethyl)cyclohexanecarboxylate (SMCC), N-succinimidyl 4-(N-maleimidomethyl)-cyclohexan-1-carboxy-(6-amidocaproate) (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl 6-(β-maleimidopropionamido) hexanoate (SMPH), N-succinimidyl 4-(p-maleimidophenyl) butylate (SMPB), N-(p-maleimidophenyl)isocyanate (PMPI), 6-maleimidocaproyl (MC), maleimidopropanoyl (MP), p-aminobenzyloxycarbonyl (PAB), N-succinimidyl 4-(2-pyridylthio)pentanoate (SPP) and N-succinimidyl (4-iodo-acetyl)aminobenzoate (SIAB), but examples are not limited thereto. Moreover, the linker may be a peptide linker such as valine-citrulline (Val-Cit) or alanine-phenylalanine (ala-phe), or the above-listed linkers may be appropriately used in combination.

With regard to a method of binding a drug to an antibody, such a drug can be bound to an antibody according to the methods described, for example, in Cancer Research; 68(22) 9280 (2008), Nature Biotechnology; 26(8) 925 (2008), Bio Conjugate Chemistry; 19, 1673 (2008), Cancer Research; 68(15) 6300 (2008), JP Patent Publication (Kohyo) No. 2008-516896 A, etc.

The toxin may be what is called immunotoxin, in which a toxin is allowed to bind to the antibody in a chemical or genetically engineering manner. Examples of the toxin include diphtheria toxin A chain, *Pseudomonas* endotoxin, ricin chain, no sugar chain ricin A chain, gelonin, and saporin.

As a radioactive substance used herein, a radioactive substance known to a person skilled in the art can be used. Examples of such a radioactive substance include yttrium 90 ($^{90}$Y), rhenium 186 ($^{186}$Re), rhenium 188 ($^{188}$Re), copper 67 ($^{67}$Cu), iron 59 ($^{59}$Fe), strontium 89 ($^{89}$Sr), gold 198 ($^{198}$Au), mercury 203 ($^{203}$Hg), lead 212 ($^{212}$Pb), dysprosium 165 ($^{165}$Dy), ruthenium 103 ($^{103}$Ru), bismuth 212 ($^{212}$Bi), bismuth 213 ($^{213}$Bi), holmium 166 ($^{166}$Ho), samarium 153 ($^{153}$Sm), and lutetium 177 ($^{177}$Lu). Preferred radioactive substances are $^{90}$Y, $^{153}$Sm, and $^{177}$Lu.

The binding of such a radioactive substance to the antibody can be carried out by a method known to a person skilled in the art (Bioconjug Chem. 1994 March-April; 5(2): 101-4.).

Cancer therapy, which uses an antibody to which a compound containing a radioisotope is bound, can be carried out by a method known to a person skilled in the art (Bioconjug Chem. 1998 November-December; 9(6): 773-82.). Specifically, at first, an antibody to which a radioisotope-containing compound has been bound is administered in a small amount to a patient, and scintigraphy is then performed on the entire body of the patient. It is confirmed that the binding level of cells in normal tissues to the antibody is low, and that the binding level of cancer cells to the antibody is high. Thereafter, the antibody to which the radioisotope-containing compound has been bound is administered in a large amount to the patient.

A preparation, which comprises a pharmaceutical composition containing the anti-human TfR antibody of the present invention, is also included in the scope of the present invention. Such a preparation preferably comprises a physiologically acceptable diluent or carrier, as well as the pharmaceutical composition containing the antibody. The preparation may also be a mixture with another antibody, or with another drug such as an anticancer agent. Examples of a suitable carrier used herein include a normal saline, a phosphate buffered saline, a phosphate buffered saline with glucose, and a buffered saline, but examples are not limited thereto. Otherwise, the antibody is freeze-dried, and when needed, the aforementioned buffered aqueous solution may be added thereto to reconstitute the antibody, and the thus reconstituted antibody may be then used. Examples of the dosage form of the preparation include: oral administration, which uses a tablet, a capsule, a granule, a powder agent, a syrup, etc.; and parenteral administration, which includes injections (subcutaneous injection, intravenous injection, intramuscular injection, intraperitoneal injection, etc.), percutaneous administration, transmucosal administration, transnasal administration, transpulmonary administration, the use of a suppository, etc. The preparation comprising the pharmaceutical composition of the present invention may be administered alone, or it may also be used in combination with other drugs.

The applied dose of the pharmaceutical composition of the present invention is different depending on symptom, age, body weight, etc. In general, in the case of oral administration, the present pharmaceutical composition is administered at a dose of approximately 0.01 mg to 1,000 mg per day per adult, in terms of the amount of an antibody contained therein. Such a dose can be administered once or divided over several administrations per day. On the other hand, in the case of parenteral administration, the present pharmaceutical composition can be administered at a dose of approximately 0.01 mg to 1,000 mg for a single administration via subcutaneous injection, intramuscular injection or intravenous administration.

The present invention will be described more in detail in the following examples. However, these examples are not intended to limit the scope of the present invention.

EXAMPLES

Example 1

Screening for Phage Antibody Using Cancer Cell Line (1) Screening for Phage Antibody Bound to Cancer Cells (Hepatic Cancer Cell Line HepG2)

HepG2 cells were cultured in 15-cm dish, and then, using 2 mg/mL collagenase I/cell dissociation buffer (Gibco BRL), the cultured cells were then removed from the dish. The cells were recovered and were then washed with cooled PBS. Thereafter, a human antibody phage library ($1\times10^{13}$ cfu) (see JP Patent Publication (Kokai) No. 2005-185281 A, WO2008/007648, and WO2006/090750) was added to the cells, and a reaction solution (1% BSA, 0.1% NaN3, and MEM) was then added thereto to a final volume of 1.6 mL. The obtained mixture was slowly rotated at 4° C. for 4 hours for performing a reaction. After completion of the reaction, the reaction solution was divided into two aliquots, and 0.6 mL of an organic solution (dibutyl phthalate and cycloheximide (9:1)) was added to each aliquot, and the thus obtained mixture was then centrifuged (300 rpm) for 2 minutes using a microcentrifuge. Thereafter, the supernatant was discarded, and cells precipitated at the bottom of the tube were suspended in 0.7 mL of 1% BSA/MEM. Then, 0.7 mL of an organic solvent was further added to the suspension. Centrifugation was carried out in the same manner as described above, and the supernatant was then discarded. The cells were suspended in 0.3 mL of PBS, followed by freezing with liquid nitrogen.

The frozen cells were thawed at 37° C., and were then infected with 20 mL of *Escherichia coli* DH12S (OD0.5) for 1 hour. The phage-infected *Escherichia coli* was placed in 600 mL of a 2×YTGA medium (2×YT, 200 μg/mL ampicisulfate, and 1% glucose), and it was then cultured at 30° C. overnight. Thereafter, 10 mL of the culture was placed into 200 mL of a 2×YTA medium (2×YT and 200 μg/mL ampicisulfate), and it was then cultured at 37° C. for 1.5 hours. Then, $1\times10^{11}$ helper phage KO7 was added to the culture, and the obtained mixture was further cultured at 37° C. for 1 hour. Subsequently, 800 mL of a 2×YTGAK medium (2×YT, 200 μg/mL ampicisulfate, 0.05% glucose, and 50 μg/mL kanamycin) was added to the culture, and the obtained mixture was then cultured at 30° C. overnight. Thereafter, the supernatant was recovered by centrifugation (8000 rpm) for 10 minutes. To the recovered supernatant, 200 mL of a PEG solution (20% polyethylene glycol 6000 and 2.5M NaCl) was added, and the obtained mixture was fully stirred. Thereafter, the reaction mixture was subjected to centrifugation (8000 rpm) for 10 minutes to precipitate phages. The phages were suspended in 10 mL of PBS. The obtained solution was defined as phages obtained from the $1^{st}$ screening.

Subsequently, the $2^{nd}$ screening was carried out. The cultured cells ($2\times10^{7}$) were mixed with the phages from the $1^{st}$ screening ($1\times10^{10}$), and a reaction solution (1% BSA, 0.1% NaN3, and MEM) was added to the mixture to a final volume of 0.8 mL. Thereafter, the same operations as those in the aforementioned $1^{st}$ screening were carried out, so as to obtain phages from the $2^{nd}$ screening.

The $3^{rd}$ screening was carried out using the phages ($1\times10^{9}$) obtained from the $2^{nd}$ screening in the same manner as described above.

(2) Analysis of Phage Antibodies

The phages obtained from the $3^{rd}$ screening were recovered, and the DNA sequences thereof were then analyzed by the existing method. Incomplete antibodies comprising deletions in the regions or antibodies having overlapping sequences were removed, so that phage antibodies each having an independent antibody sequence could be obtained (see Japanese Patent No. 4870348).

By the same method, phage antibodies reacting with cancer antigens were screened using 21 types of cancer cells shown in the following Table 1. As a result, 1863 phage antibodies each having an independent sequence were obtained, as shown in Table 1.

TABLE 1

| Cancer cells | Number of obtained phages |
|---|---|
| CO-2 | 102 |
| MKN45 | 90 |
| OCTH-16 | 82 |
| HepG2 | 410 |
| NCI-H441 | 80 |
| K562 | 33 |
| U937 | 107 |
| HL-60 | 107 |
| MV4-11 | 46 |
| KF28 | 62 |
| NCI-N87 | 50 |
| RERF-LC-AI | 73 |
| SW480 | 46 |
| MCF7 | 73 |
| LNCap.FGC | 60 |
| MDA-MB-231 | 78 |
| U-87MG | 62 |
| T98G | 71 |
| DU-145 | 96 |
| MMAc | 76 |
| G-361 | 59 |

Example 2

Screening for Phages Reacting with Soluble Human TfR (1) Production of Soluble TfR Antigen-Generating Cells Using cancer cell lines MIAPaCa2 and SKOV-3, the cDNA of TfR was produced by a PCR method. The cDNA of a TfR extracellular domain was prepared by an ordinary method, and the prepared cDNA was then inserted into pCMV-Script (manufactured by Clontech) to produce a soluble TfR antigen expression vector. This expression vector was introduced into a cell line 293T, so as to produce cells generating a soluble TfR antigen.

(2) Screening for Positive Phages by ELISA

A supernatant of the above described soluble TfR-generating cells was recovered, and it was then purified to obtain a soluble TfR antigen. Using this soluble TfR antigen, the reactivity of antigen-antibody was examined by ELISA. Specifically, the concentration of the soluble TfR antigen was adjusted to be 10 μg/mL with PBS, and it was then added to Immuno Module/Strip Plates (NUNK) to a volume of 50 μL/well. It was left at rest at 37° C. for 2 hours. Thereafter, the soluble TfR antigen was discarded, and a blocking solution (5% skimmed milk/0.05% NaN3/PBS) was added thereto to a volume of 200 μL/well, followed by performing blocking at 37° C. for 2 hours. Thereafter, the blocking solution was removed, and the residue was then washed with PBS. The culture supernatant of the abovementioned phage (Table 1) was added to each well to a volume of 100 µL/well, and it was then reacted at 37° C. for 1 hour. The plate was washed with PBS five times, and 1 µg/mL Rabbit anti-cp3 that had been diluted with PBS/0.05% Tween20 was then added to the plate to a volume of 100 µL/well. The thus obtained mixture was reacted at 37° C. for 1 hour. The plate was washed with PBS five times, and anti-Rabbit IgG (H+ L)-HRP that had been 2000 times diluted with PBS/0.05% Tween20 was further added to the plate to a volume of 100 µL/well. The thus obtained mixture was reacted at 37° C. for 1 hour. The plate was washed with PBS five times, and OPD in a 0.1 M citrate phosphate buffer (pH 5.1)+0.01% $H_2O_2$ was then added thereto to a volume of 100 µL/well. The obtained mixture was reacted at room temperature for 5 minutes. Thereafter, $2NH_2SO_2$ was added to the reaction solution to a volume of 100 µL/well, so as to terminate the coloring reaction. Subsequently, the absorbance at 492 nm was measured using SPECTRA max340PC (Molecular Devices). As a result, twenty strains of phages exhibiting a significant positive reaction to the soluble TfR antigen were found in the 1863 strains of phages. The DNA sequences of these 20 strains of phages were analyzed, and as a result, it was confirmed that all of their CDR sequences were novel. The CDR sequences are as follows.

(1) TfR001 Antibody
VH CDR1: SEQ ID NO: 1, VH CDR2: SEQ ID NO: 2, VH CDR3: SEQ ID NO: 3
VL CDR1: SEQ ID NO: 4, VL CDR2: SEQ ID NO: 5, VL CDR3: SEQ ID NO: 6

(2) TfR002 Antibody
VH CDR1: SEQ ID NO: 7, VH CDR2: SEQ ID NO: 8, VH CDR3: SEQ ID NO: 9
VL CDR1: SEQ ID NO: 10, VL CDR2: SEQ ID NO: 11, VL CDR3: SEQ ID NO: 12

(3) TfR003 Antibody
VH CDR1: SEQ ID NO: 13, VH CDR2: SEQ ID NO: 14, VH CDR3: SEQ ID NO: 15
VL CDR1: SEQ ID NO: 16, VL CDR2: SEQ ID NO: 17, VL CDR3: SEQ ID NO: 18

(4) TfR004
VH CDR1: SEQ ID NO: 19, VH CDR2: SEQ ID NO: 20, VH CDR3: SEQ ID NO: 21
VL CDR1: SEQ ID NO: 22, VL CDR2: SEQ ID NO: 23, VL CDR3: SEQ ID NO: 24

(5) TfR005
VH CDR1: SEQ ID NO: 25, VH CDR2: SEQ ID NO: 26, VH CDR3: SEQ ID NO: 27
VL CDR1: SEQ ID NO: 28, VL CDR2: SEQ ID NO: 29, VL CDR3: SEQ ID NO: 30

(6) TfR006
VH CDR1: SEQ ID NO: 31, VH CDR2: SEQ ID NO: 32, VH CDR3: SEQ ID NO: 33
VL CDR1: SEQ ID NO: 34, VL CDR2: SEQ ID NO: 35, VL CDR3: SEQ ID NO: 36

(7) TfR007
VH CDR1: SEQ ID NO: 37, VH CDR2: SEQ ID NO: 38, VH CDR3: SEQ ID NO: 39
VL CDR1: SEQ ID NO: 40, VL CDR2: SEQ ID NO: 41, VL CDR3: SEQ ID NO: 42

(8) TfR008
VH CDR1: SEQ ID NO: 43, VH CDR2: SEQ ID NO: 44, VH CDR3: SEQ ID NO: 45
VL CDR1: SEQ ID NO: 46, VL CDR2: SEQ ID NO: 47, VL CDR3: SEQ ID NO: 48

(9) TfR009
VH CDR1: SEQ ID NO: 49, VH CDR2: SEQ ID NO: 50, VH CDR3: SEQ ID NO: 51
VL CDR1: SEQ ID NO: 52, VL CDR2: SEQ ID NO: 53, VL CDR3: SEQ ID NO: 54

(10) TfR010
VH CDR1: SEQ ID NO: 55, VH CDR2: SEQ ID NO: 56, VH CDR3: SEQ ID NO: 57
VL CDR1: SEQ ID NO: 58, VL CDR2: SEQ ID NO: 59, VL CDR3: SEQ ID NO: 60

(11) TfR011
VH CDR1: SEQ ID NO: 61, VH CDR2: SEQ ID NO: 62, VH CDR3: SEQ ID NO: 63
VL CDR1: SEQ ID NO: 64, VL CDR2: SEQ ID NO: 65, VL CDR3: SEQ ID NO: 66

(12) TfR012
VH CDR1: SEQ ID NO: 67, VH CDR2: SEQ ID NO: 68, VH CDR3: SEQ ID NO: 69
VL CDR1: SEQ ID NO: 70, VL CDR2: SEQ ID NO: 71, VL CDR3: SEQ ID NO: 72

(13) TfR013
VH CDR1: SEQ ID NO: 73, VH CDR2: SEQ ID NO: 74, VH CDR3: SEQ ID NO: 75
VL CDR1: SEQ ID NO: 76, VL CDR2: SEQ ID NO: 77, VL CDR3: SEQ ID NO: 78

(14) TfR014
VH CDR1: SEQ ID NO: 79, VH CDR2: SEQ ID NO: 80, VH CDR3: SEQ ID NO: 81
VL CDR1: SEQ ID NO: 82, VL CDR2: SEQ ID NO: 83, VL CDR3: SEQ ID NO: 84

(15) TfR015
VH CDR1: SEQ ID NO: 85, VH CDR2: SEQ ID NO: 86, VH CDR3: SEQ ID NO: 87
VL CDR1: SEQ ID NO: 88, VL CDR2: SEQ ID NO: 89, VL CDR3: SEQ ID NO: 90

(16) TfR016
VH CDR1: SEQ ID NO: 91, VH CDR2: SEQ ID NO: 92, VH CDR3: SEQ ID NO: 93
VL CDR1: SEQ ID NO: 94, VL CDR2: SEQ ID NO: 95, VL CDR3: SEQ ID NO: 96

(17) TfR017
VH CDR1: SEQ ID NO: 97, VH CDR2: SEQ ID NO: 98, VH CDR3: SEQ ID NO: 99
VL CDR1: SEQ ID NO: 100, VL CDR2: SEQ ID NO: 101, VL CDR3: SEQ ID NO: 102

(18) TfR018
VH CDR1: SEQ ID NO: 103, VH CDR2: SEQ ID NO: 104, VH CDR3: SEQ ID NO: 105
VL CDR1: SEQ ID NO: 106, VL CDR2: SEQ ID NO: 107, VL CDR3: SEQ ID NO: 108

(19) TfR019
VH CDR1: SEQ ID NO: 109, VH CDR2: SEQ ID NO: 110, VH CDR3: SEQ ID NO: 111
VL CDR1: SEQ ID NO: 112, VL CDR2: SEQ ID NO: 113, VL CDR3: SEQ ID NO: 114

(20) TfR020
VH CDR1: SEQ ID NO: 115, VH CDR2: SEQ ID NO: 116, VH CDR3: SEQ ID NO: 117
VL CDR1: SEQ ID NO: 118, VL CDR2: SEQ ID NO: 119, VL CDR3: SEQ ID NO: 120

SEQ ID NO: 1:
TSGVGVG

SEQ ID NO: 2:
LIYWDDDKHYSPSLKS

SEQ ID NO: 3:
NGDYGIEFDY

SEQ ID NO: 4:
GGNNIGSKSVH

SEQ ID NO: 5:
YDSDRPS

SEQ ID NO: 6:
QVWDSSSDHVV

SEQ ID NO: 7:
SYSMN

SEQ ID NO: 8:
SISSSSSYIYYADSVKG

SEQ ID NO: 9:
ARESVDAFDI

SEQ ID NO: 10:
QGDSLRSYDAS

SEQ ID NO: 11:
GLSDRPS

SEQ ID NO: 12:
ISRDSGGNPH

SEQ ID NO: 13:
SYAMS

SEQ ID NO: 14:
AISGSGGSTYYADSVKG

SEQ ID NO: 15:
GYYGSNYYYGMDV

SEQ ID NO: 16:
SGSSSNIGSNYVY

SEQ ID NO: 17:
RNNQRPS

SEQ ID NO: 18:
AAWDDSLSGPV

SEQ ID NO: 19:
DFVFS

SEQ ID NO: 20:
WISAHDGNTNYAQKLQD

SEQ ID NO: 21:
DTFTNLLGDYSYDAMDV

SEQ ID NO: 22:
GSSTGAVTSGHYPY

SEQ ID NO: 23:
DTTEKHS

SEQ ID NO: 24:
LLSSGDGRAV

SEQ ID NO: 25:
NYGMS

SEQ ID NO: 26:
WISAYNGNTNYGEKLQG

SEQ ID NO: 27:
DDYYGSGVDAFDI

SEQ ID NO: 28:
GGNKIGSKSVH

SEQ ID NO: 29:
YDRDRPS

SEQ ID NO: 30:
QVWDSSSDVV

SEQ ID NO: 31:
SYGMH

SEQ ID NO: 32:
VISFDGSSKYYADSVKG

SEQ ID NO: 33:
DSNFWSGYYSPVDV

SEQ ID NO: 34:
TRSSGSIASNSVQ

SEQ ID NO: 35:
YEDTQRPS

SEQ ID NO: 36:
QSYDSAYHWV

SEQ ID NO: 37:
SYWLS

SEQ ID NO: 38:
KIDPSDSYTQYSPSFEG

SEQ ID NO: 39:
HGYDAFHV

SEQ ID NO: 40:
SGSSSNIGNNAVN

SEQ ID NO: 41:
YDDLLPS

SEQ ID NO: 42:
AAWDDSLNGWV

SEQ ID NO: 43:
DYAMH

SEQ ID NO: 44:
GISWNSGSIGYADSVKG

SEQ ID NO: 45:
DQHREFYYYGMDV

SEQ ID NO: 46:
SGSSSNIGSNYVY

SEQ ID NO: 47:
RNNQRPS

SEQ ID NO: 48:
AAWDDSLSGPV

SEQ ID NO: 49:
SYWIG

SEQ ID NO: 50:
IIYPGDSDTRYSPSFQG

SEQ ID NO: 51:
QGTNWGVGDAFDI

SEQ ID NO: 52:
GGNNIGSKSVH

SEQ ID NO: 53:
DDSDRPS

SEQ ID NO: 54:
QVWDISSDHVV

SEQ ID NO: 55:
SYAMS

SEQ ID NO: 56:
AISGSGGSTYYADSVKG

SEQ ID NO: 57:
DRYYYGSGSYYDAFDI

-continued

SEQ ID NO: 58:
QGDSLRSYYAS

SEQ ID NO: 59:
GKNNRPS

SEQ ID NO: 60:
NSRDSSGNHVV

SEQ ID NO: 61:
SYSMN

SEQ ID NO: 62:
VISYDGSNKYYADSVKG

SEQ ID NO: 63:
VDPGDRGWYFDL

SEQ ID NO: 64:
SGSSSNIGSNTVN

SEQ ID NO: 65:
SNNQRPS

SEQ ID NO: 66:
AAWDDSLNGWV

SEQ ID NO: 67:
SSPYYWG

SEQ ID NO: 68:
SVYYSGNTYYNPSLTR

SEQ ID NO: 69:
HSWGINDAFDV

SEQ ID NO: 70:
SGSSSNIGNNYVS

SEQ ID NO: 71:
DNNKRPS

SEQ ID NO: 72:
GTWDSSLSVWV

SEQ ID NO: 73:
DYAMH

SEQ ID NO: 74:
GISWNSGSIDYADSVKG

SEQ ID NO: 75:
ENLAVAGLDY

SEQ ID NO: 76:
QGDSLRGYYAS

SEQ ID NO: 77:
DKNTRPS

SEQ ID NO: 78:
QSRDNSGEMVV

SEQ ID NO: 79:
ELSMH

SEQ ID NO: 80:
GFDPEDGETIYAQKFQG

SEQ ID NO: 81:
DAYYGSGSPRDAFDI

SEQ ID NO: 82:
GGDNVGGKSLH

SEQ ID NO: 83:
DDRDRPS

SEQ ID NO: 84:
QVWDDISRLVI

-continued

SEQ ID NO: 85:
SYYIH

SEQ ID NO: 86:
IINPRGGGTDFAQKFQG

SEQ ID NO: 87:
GDCTNGVCYSGGLDV

SEQ ID NO: 88:
SGSSSNIGNNYVS

SEQ ID NO: 89:
DNDKRPS

SEQ ID NO: 90:
GTWDNSLSGV

SEQ ID NO: 91:
DYAMH

SEQ ID NO: 92:
GISWNSGSIGYADSVKG

SEQ ID NO: 93:
DVDLWFGEYYFDY

SEQ ID NO: 94:
SGSSSNIGNNYVS

SEQ ID NO: 95:
DNNKRPS

SEQ ID NO: 96:
GTWDSSLSAPYV

SEQ ID NO: 97:
DYAMY

SEQ ID NO: 98:
GINWNSAIIGYADSVKG

SEQ ID NO: 99:
EALYYSAFFDS

SEQ ID NO: 100:
SGSSSNIGNNYVS

SEQ ID NO: 101:
DNNKRPS

SEQ ID NO: 102:
GTWDSSLSAWV

SEQ ID NO: 103:
DYAMH

SEQ ID NO: 104:
GINWNGGSTDYADSVEG

SEQ ID NO: 105:
DYADLGSGSDY

SEQ ID NO: 106:
SGSRSNIGSNYVH

SEQ ID NO: 107:
RNDQRPS

SEQ ID NO: 108:
ASWDDKMSGRL

SEQ ID NO: 109:
SYEMN

SEQ ID NO: 110:
YISSSGSTIYYADSVKG

SEQ ID NO: 111:
HSNYDILTGYSTDAFDI

-continued

SEQ ID NO: 112:
TGTSSDIGFYDSVS

SEQ ID NO: 113:
DVSNRPS

SEQ ID NO: 114:
TSNTKTNTLYV

SEQ ID NO: 115:
RGNYWWT

SEQ ID NO: 116:
SVHYSGSTNYNPSLKS

SEQ ID NO: 117:
DSDYGDYYFDY

SEQ ID NO: 118:
QGDSLRSYYAS

SEQ ID NO: 119:
GKNNRPS

SEQ ID NO: 120:
NSRDSSGNHVV

Example 3

Confirmation of Reactivity of Anti-TfR Phage Antibodies with TfR (1) Immunoprecipitation Further, in order to confirm that the aforementioned 20 types of phage antibodies recognize human TfR, immunoprecipitation and Western blotting were carried out. The 20 types of phages were transmitted to *Escherichia coli*, and each culture supernatant was then recovered and purified to obtain a purified scFv antibody. 5 mg of the antibody was immobilized with respect to 1 ml of CNBr-activated sepharose 4B in Glass Filter, so as to produce antibody beads. Subsequently, SKOV-3 cells cultured in a 10-cm³ dish were recovered to prepare 600 μL of a cell lysate. 60 μL of biotin was added to 600 μL of the cell lysate to biotinylate the antigen. 150 μL of a solution of the produced antibody beads and the biotinylated cell lysate were placed in a 2-mL tube, and the obtained mixture was then stirred at 4° C. for 6 hours. Thereafter, the tube was subjected to centrifugation (5500 g, 1 minute, 4° C.), and the supernatant was then removed. Then, 800 μL of a washing buffer (0.5 mM Biotin and 0.1% Tween20/PBS) was added into the tube, and the beads were then washed by centrifugation. The beads were repeatedly washed three times, and 30 μL of a citric acid solution for elution (50 mM citric acid, pH 2.5) was then added thereto, followed by stirring and then centrifugation (5,500 g, 1 minute, 4° C.). An immune complex was eluted by recovering the supernatant. Such an elution operation was repeatedly performed three times, and the supernatant was recovered. It was neutralized by addition of 3 M Tris, and was then electrophoresed by SPS-PAGE. Then, a band was confirmed by silver staining. This sample was simultaneously subjected to Western blotting using streptavidin-HRP (Anti-Streptavidin, IgG Fraction, Conjugated to Peroxidase, CORTEX Biochem). As a result, as shown in FIG. 1, it was confirmed that each antibody (TfR001, TfR003, and TfR005) bound to a protein with a molecular weight of approximately 90 KD (the molecular weight of TfR: approximately 90 KD).

(2) Mass Spectrometry

Subsequently, the antigen protein obtained by the immunoprecipitation method was subjected to mass spectrometry. The detected portion corresponding to a membrane protein was digested by trypsin in gel, and a peptide was then recovered. SDS polyacrylamide gel electrophoresis was carried out according to an ordinary method, and the resultant was then strained with Coomassie brilliant blue. The obtained band was excised from the gel. The band was immersed in a 200 mM ammonium bicarbonate-50% acetonitrile solution, and the solution was then shaken at 37° C. for 45 minutes. Thereafter, the solution was discarded, and the same operation was repeatedly carried out twice to remove Coomassie brilliant blue. The gel was dried under reduced pressure, and to the resulting gel, trypsin (20 μg/mL) dissolved in 40 mM ammonium bicarbonate (pH 8.1)-10% acetonitrile was added in an amount of 4 μL per unit area (mm2) of the sliced gel. The obtained mixture was left at room temperature for 1 hour for sufficient infiltration. A trypsin solution was added to the resultant in an amount 2.5 times larger than the previously added trypsin solution, and the obtained mixture was then left at rest at 37° C. for 18 hours. Thereafter, the reaction product was filtrated with a filter tube with a pore size of 0.22 μm, so as to recover a peptide generated by destroying the antigen by trypsin.

The sample obtained by the in-gel trypsin digestion was subjected to HPLC that was connected with electrospray ionization ion-trap quadrupole mass spectrometer. Individual peptides were successively eluted from a reverse-phase chromatographic column of the HPLC due to a difference in hydrophobicity, as a result of a change in the linear concentration gradient of 0%-80% acetonitrile containing 0.1% TFA. Such peptides were ionized by an electrospray method, and the mass of each peptide and the internal amino acid sequence thereof were then determined. A set of the obtained internal amino acid sequences was searched against the database of the published TfR amino acid sequences. As a result, it was confirmed that the phage antibody binds to TfR.

Example 4

Preparation of IgG from Phage Antibody (scFv)

(1) Construction of Plasmid Expressing TfR006 IgG Antibody

Construction of IgG expression vector from a phage antibody will be explained below, using the preparation of IgG from TfR006 as an example. IgG expression vector was constructed from each of other antibodies in the same manner as described below.

The genes of the phage antibody (scFv) of TfR006 are aligned in the order of VH-VL. Such VH and VL are connected with each other by a linker (SEQ ID NO: 121) and have the structure of scFv.

Figure 2:
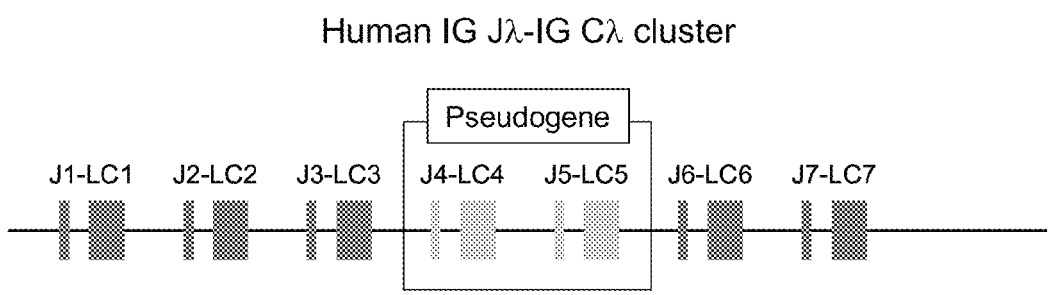
FIG. 2 shows human antibody genes. In a human antibody gene light chain λ, five J chain (junction) genes and five C chain (constant) genes are present in parallel in the order of J and C. J4-LC4 and J5-LC5 are pseudogenes, and do not function.

VH is constituted with three genes V, D and J, whereas VL is constituted with two genes V and J. In the case of the human light chain λ, five sets of Jλ (λ Junction) genes and Cλ (λ constant) genes are aligned in parallel, and J4-CL4 and J5-CL5 are pseudogenes (FIG. 2).

The results obtained by searching in IMGT (*) for human germ line genes assumed to be used in the VH and VL of TfR006 are shown in Table 2.

(*) IMGT: http://www.imgt.org

TABLE 2

| VH | IGHV3-30 or IGHV3-33 | IGHJ6 | IGHD3-3 |
|---|---|---|---|
| VL | IGLV6-57 | IGLJ3 | |

Referring to the results of the IMGT search, IgG gene was constructed from the phage antibody. A gene, in which TfR006VH is connected with the constant region (SEQ ID NO: 122) of human G1 and TfR006VL is connected with IGLC3 (SEQ ID NO: 123) that is aligned in parallel with the IGL J3 gene, was totally synthesized by GenScript. Upon the artificial synthesis of a full-length gene, optimization of codon usage was carried out (in accordance with the method described in Kim et al., Codon optimization for high-level expression of human erythropoietin in mammalian cells, Gene, Vol 199, 1997, pp. 293-301), and a DNA sequence for efficient translation (Kozak, At least six nucleotides preceding the AUG initiator codon enhance translation in mammalian cells, J Mol Biol Vol 196, pp. 947-950, 1987), and the consensus sequence (SEQ ID NO: 124) of the signal peptide of the human antibody heavy chain subgroup 3, were added to the 5'-terminal sides of the heavy chain and light chain genes as secretory signals. In addition, with regard to the both termini of heavy chain and light chain genes to be synthesized, NheI was added to the 5'-terminal side thereof and EcoRI was added to the 3'-terminal side thereof for insertion into an expression vector.

pCAGGS (Niwa et al., Efficient selection for high-expression transfectants with a novel eukaryotic vector, Gene, Vol 108, pp. 193-200) was used as an expression vector for antibody genes. A mouse DHFR gene expression region was inserted into the HindIII site of this vector for gene amplification.

(2) Transient Expression of TfR006 IgG Antibody

FreeStyle (Life Technologies) was used for transient expression of a TfR006 IgG antibody. 293-F (Life Technologies) used as floating cells for gene transfection was subcultured the day before transfection. On the day of transfection, 400 mL of a cell suspension whose cell density had been adjusted to be $1 \times 10^6$ cells/mL was prepared. Solution I was prepared by suspending a total of 200 μg of plasmid (100 μg of a TfR006 heavy chain expression vector and 100 μg of a TfR006 light chain expression vector) in OptiPro SFM. Subsequently, 200 μL of MAX reagent was added to 8 mL of OptiPRO (Solution II). Solution (I) was mixed with Solution (II), and the mixed solution was then left at rest at room temperature for 10 to 20 minutes. A total of 16 mL of the reaction solution was added to 400 mL of a 293 expression medium, in which the 293-F cells had been suspended, and the obtained mixture was then cultured at 37° C. in 8% $CO_2$ for 6 to 7 days, using a cell culture shaker TAITEC BioShaker BR-43FL. After 6 to 7 days of the culture, a culture supernatant containing a recombinant TfR006 antibody was recovered and was used as a material for purification.

(3) Establishment of a Cell Line Stably Producing TfR006 IgG Antibody

CHO dhfr(−) cells (G. Urlaub et al., Isolation of Chinese hamster cell mutants deficient in dihydrofolate reductase activity, Proc. Natl. Acad. Sci. USA 77, pp. 4216-4220, 1980) were used in simultaneous transformation with two types of plasmids (wherein a plasmid was cleaved with PvuI in an ampicillin resistance gene to form linear plasmids from a circular plasmid), that is pCAGGS-IGL-CMV-dhfr-A vector used for expression of a TfR 006 L chain and pCAGGS-IGH-CMV-dhfr-A vector used for expression of a TfR 006 H chain. Electroporation was carried out using Amaxa manufactured by LONZA. DNA (0.002 mg/sample for each plasmid of L chain and H chain) was added to 0.1 mL of Amaxa electroporation CHO buffer containing $3 \times 10^3$ cells, and electric pulse was then given thereto.

The cells treated by electroporation were added to an Iscove's Modified Dulbecco Medium (IMDM), which contained 10% dialyzed FBS and did not contain HT (H: hypoxanthine; T: thymidine). Three days after the gene transfection, the medium was replaced with IMDM, which did not contain 10% dialyzed FBS, 2 mM L-glutamine and HT. Thereafter, the transfected neo+ cells were selected with 1 mg/mL G418, and clones of TfR006 IgG antibody production-positive cell line were obtained. Subsequently, gene amplification was carried out using the clones selected with G418. The gene was amplified in 2 rounds of methotrexate (MTX) (0.25 mM, 1 mM), and a cell line capable of producing approximately 50 mg of TfR006 IgG antibody per liter was established.

(4) Purification of TfR006 IgG Antibody

A TfR006 IgG antibody protein contained in a culture supernatant of a cell line transiently expressing the TfR006 IgG antibody, or in a culture supernatant of a cell line stably expressing the TfR006 IgG antibody, was purified using an Ab-Capcher ExTra (ProteNova) affinity column with AKTAprime. The obtained peak fraction was subjected to gel filtration using a Sephacryl S-300 column that had been equilibrated with Dalbecco's PBS as a solvent, so as to further purify it. The purified TfR006 IgG antibody protein was quantified using an absorption coefficient. The absorption coefficient of the TfR006 IgG antibody was calculated using the total amino acid sequences of TfR006 in ProtParam (http://web.expasy.org/protparam/) of EXPASY. As a result, $\epsilon = 1.607$ was obtained.

(5) Quantification of TfR006 IgG Antibody by Enzyme-Linked Immunosorbent Assay (ELISA)

The concentration of an antibody contained in a culture supernatant of TfR006 IgG antibody-producing cells or a purified antibody was quantified based on absorbance, and was also quantified by enzyme-linked immunosorbent assay (ELISA). As a solid-phase antibody, goat anti-human IgG (H+L) (which had previously been absorbed against mouse, rabbit, bovine, and mouse IgG) (COMSO BIO: American Qualex International, Inc.; AQI, Cat. No. A-110UD) was added in an amount of 100 μl/well (concentration: 5 μg/mL) to a plate, and it was then left at rest at 4° C. over a day and a night. Subsequently, Block Ace was added in an amount of 200 μL/well to the plate to carry out blocking at room temperature for 1 hour. Thereafter, the antibody as a sample was subjected to serial dilution, and it was then added to each well, followed by incubation for 1 hour for performing a reaction. The reaction product was washed with PBST (0.05% Tween20 and PBS) five times, and then, a detection antibody solution which was prepared by diluting goat anti-human IgG (H+L) (absorbed against mouse, rabbit, bovine, and mouse IgG)-HRP (COSMO BIO: AQI, Cat. A-110PD) by 10,000 times with PBST, was added in an amount of 100 μL/well to the resultant. The obtained mixture was incubated for 1 hour, and was then washed with PBST five times. Thereafter, a substrate buffer TMB was added in an amount of 100 μL/well to the resultant. The obtained mixture was incubated at room temperature in a dark place for 15 minutes, and a reaction termination solution was then added thereto in an amount of 100 μL/well so as to terminate the reaction. Thereafter, absorbance at 450 nm was measured. Using purified human IgG as a standard product, a calibration curve was obtained, and the concentration of a human antibody was calculated using this calibration curve.

Example 5

Reactivity of TfR IgG Antibodies

Figure 3:
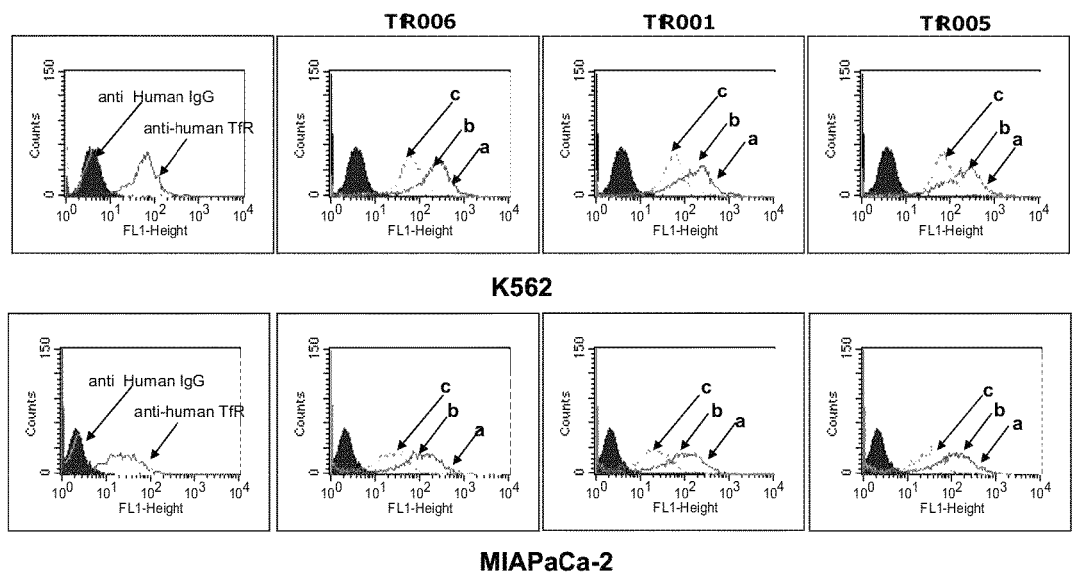
FIG. 3 shows the results of flow cytometry performed using TfR IgG antibodies and cancer cell lines.

Two cell lines of TfR-expressing cells, K562 (ATCC CCL-243: CML) and MIAPaCa-2 (ATCC CRL-1420: pancreatic cancer), were used to examine the reactivity of the anti-TfR IgG antibodies. K562 cells were recovered by centrifugation. MIAPaCa-2 was removed with 2 mM EDTA/PBS and were then recovered by centrifugation. The thus recovered cells were each washed with PBS once, and were then suspended in FACS Buffer (PBS containing 1% BSA, 2 mM EDTA, and 0.1% NaN3), resulting in a cell density of $1\times10^6$ cells/mL. 100 µL of this cell suspension was dispensed into a 96-well V bottom plate (Costar 3897). Thereafter, a TfR001 IgG antibody, a TfR005 IgG antibody, and a TfR006 IgG antibody were each adjusted to be 1 to 0.01 µg/mL with FACS Buffer, and 100 µL of each antibody solution was added to the cells. The obtained mixture was incubated at 4° C. for 1 hour. Thereafter, the resulting cells were washed with FACS Buffer twice, and 100 µL of Alexa-anti-human IgG (invitrogen) solution that had been diluted 750 times with FACS Buffer was then added to the cells. The thus obtained mixture was stirred and was then incubated at 4° C. for 1 hour. The resultant was washed by centrifugation with FACS Buffer twice, and was then equipped into HTS of FACS Calibur (BD), so as to measure the fluorescence intensity of FL1 in each well. As shown in FIG. 3, all antibodies (a: 500 ng/mL; b: 50 ng/mL; and c: 5 ng/mL) exhibited strong reactivity with K562 and MIAPaCa-2. Anti-human IgG (1 µg/mL) and anti-human TfR (1 µg/mL MBL D259-3) were used as a negative control and a positive control, respectively.

Example 6

In Vitro Growth-Suppressing Effect of TfR IgG Antibodies

Thirteen TfR-expressing cell lines, namely, Ramos (ATCC CRL-1596), K-562 (ATCC CCL-243), NCI-H358 (ATCC CRL-5807), A549 (ATCC CCL-185), MIAPaCa-2 (ATCC CRL-1420), PK-45P (Institute of Development, Aging and Cancer, Tohoku University, TKG 0493), KLM-1 (RCB), A431 (ATCC CRL-1555), DU145 (ATCC HTB-81), HT-29 (ATCC HTB-38), BFTC905 (DSMZ ACC361), MKN45 (JCRB JCRB0254) and MT-2, were each adjusted to a cell density of 2,500 to 10,000 cells/mL with a culture medium, and each cell solution was then dispensed in an amount of 100 µL/well into a 96-well flat bottom plate (NUNC 167008). The cells were then cultured at 37° C. in 5% $CO_2$ in 95% air for 24 hours. Thereafter, a dilution series of TfR006 antibody of 20 µg/mL to 1.52 ng/mL was produced, and 100 µL of the produced antibody was added to the plate during the culture. The cells were further cultured at 37° C. in 5% $CO_2$ in 95% air for 96 hours. After completion of the culture, the plate was centrifuged at 1,200 rpm for 3 minutes, and the supernatant was gently removed. Thereafter, 100 µL of PBS was added to the residue. The obtained mixture was further centrifuged. PBS was dispensed in a 96-well V bottom plate (Costar 3897), and 50 µL of 0.25% Trypsin EDTA was added thereto, so as to remove the cells. The cells were stirred by pipetting, and a total amount of the cells was transferred into a PBS-containing V bottom plate. The wells were each washed with 50 µL of the culture medium, and the total amount thereof was transferred into the V bottom plate. This V bottom plate was equipped into HTS of FACS Calibur (BD), and after stirring, 40 µL of the solution was aspirated from each well, and the number of cells contained in the total amount of the solution was then counted. The counted cell number×5 was defined as the number of cells per well. The cell growth rate upon addition of the antibody in each concentration was calculated from the calculation formula below. Using Master Plex 2010 Software (Hitachi Solutions, Ltd.), an antibody concentration exhibiting a growth rate of 50% (IC50) was obtained. As a result, all of the antibodies exhibited a strong cell growth-suppressing effect. The IC50 of each antibody is shown in Table 3.

Growth rate=Number of cells (antibody added)/number of cells (no antibody added)×100%

TABLE 3

| | | IC50 (ng/ml) | | |
| Type of Cancer | Cell Line | TfR006 | TfR001 | TfR005 |
| --- | --- | --- | --- | --- |
| Lung cancer | NCI-H358 | 37 | 59 | NT |
| | NCI-H1373 | 127 | 262 | NT |
| | A549 | 41 | 138 | NT |
| Pancreatic cancer | PK45-P | 100 | 171 | 636 |
| | MIAPaCa-2 | 55 | 153 | 630 |
| | KLM1 | 30 | 52 | 121 |
| Colon cancer | HT29 | 25 | 52 | 287 |
| Stomach cancer | MKN45 | 26 | 64 | 154 |
| Prostate cancer | DU145 | 33 | 55 | 245 |
| Bladder cancer | BFTC905 | 44 | 130 | 338 |
| Blood cancer | MT-2 | 71 | NT | NT |
| | RAMOS | 8 | 11 | NT |
| | K562 | 50 | 90 | 389 |
| Skin cancer | A431 | 36 | 145 | NT |

Example 7

Antitumor Effects on Xenograft Models

The antitumor effects of the human anti-TfR antibody on xenograft models, into which the following TfR-positively-expressing cancer cell lines had been each transplanted, were confirmed.

TABLE 4

| Cell Line | Type of Cancer | Culture Medium |
| --- | --- | --- |
| PK-45P | Pancreatic cancer | RPMI1640 + 10% FBS |
| HT-29 | Colon cancer | McCoy's5A + 10% FBS |
| K562 | Leukemia | RPMI1640 + 10% FBS |
| MIAPaCa-2 | Pancreatic cancer | DMEM + 10% FBS |
| DU145 | Prostate cancer | MEM + 10% FBS |
| RAMOS | Lymphoma | RPMI1640 + 10% FBS |
| BFTC905 | Bladder cancer | DMEM + 10% FBS |

The above-mentioned cells were cultured in each culture medium shown in Table 4 above. Upon transplantation, cells of each type were suspended in RPMI1640, and the thus obtained cancer cell suspension was then transplanted into the subcutis on the right abdomen of each SCID mouse (female, 7-week-old, CLEA Japan, Inc.), resulting in a cell density of $5\times10^6$ cells/mouse. After completion of the transplantation, the diameter of a tumor was measured with a vernier caliper, and the volume of the tumor was then obtained from the formula below. At the time point at which the mean tumor volume reached 150 $mm^3$ or more, the cancer-bearing mice of each type of cancer cell line were divided into two groups (n=5), using grouping software (EXSAS version 7.6, CLC Corporation). With regard to an antibody administration group, the TfR006 antibody diluted with PBS was administered at a dose of 15 mg/kg per mouse into the caudal vein of each mouse. With regard to a negative control group, PBS was administered at an amount of 0.2 mL/20 g mouse into the caudal vein of each mouse. Administration was carried out twice a week (every three or four days) in a total of six times. After completion of the administration, the tumor diameter was measured with a vernier caliper twice a week, and the tumor volumes in each group were obtained. Antitumor effects were determined based on such tumor volume.

Tumor volume was calculated according to the following formula.

Tumor volume=(Minor axis)$^2$×Major axis×0.5

Figure 4:
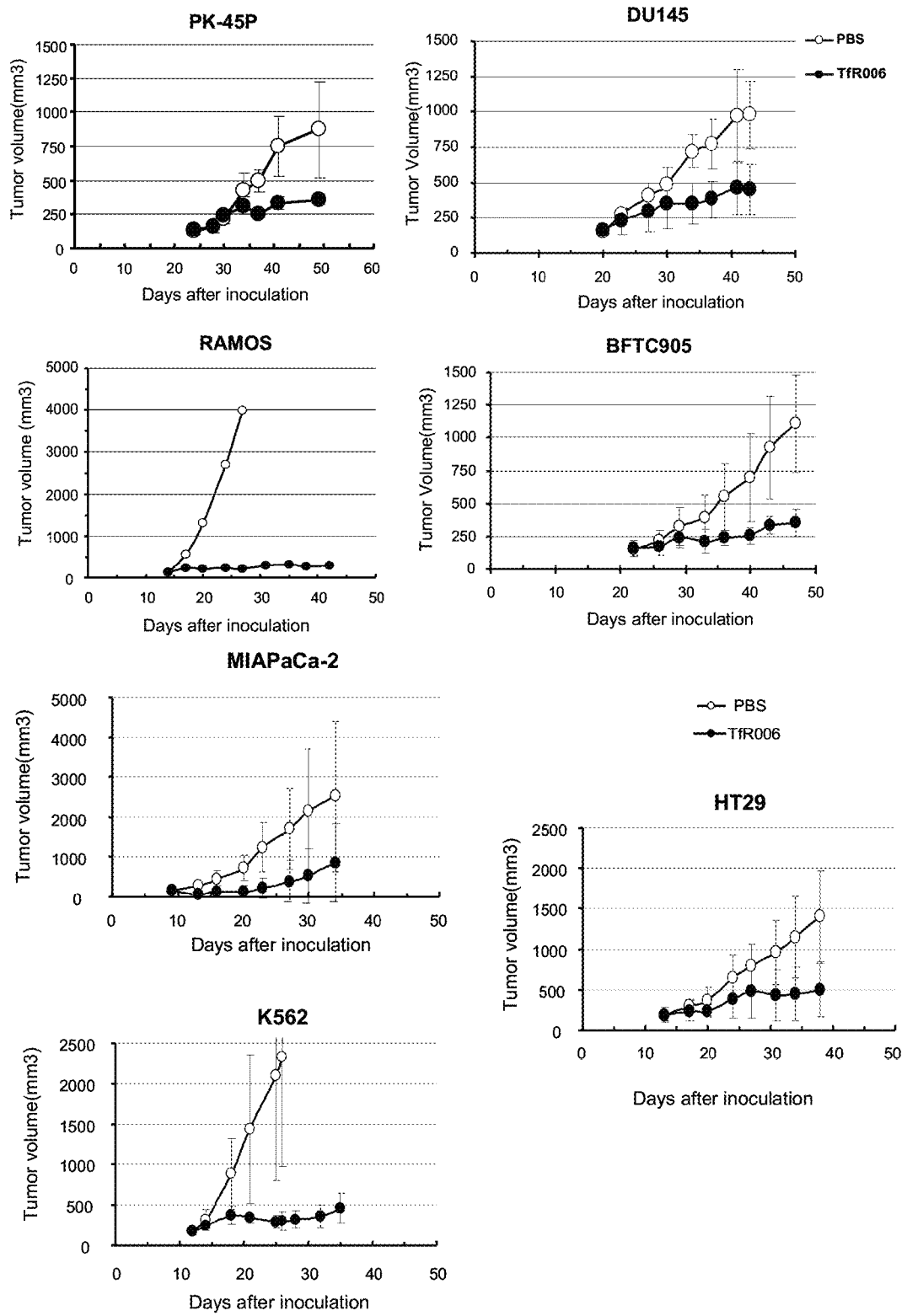
FIG. 4 shows the antitumor effects of a TfR IgG antibody on individual cancer models.

A change over time in a mean value of the tumor volumes in each group is shown in FIG. 4. With regard to all of the cancer cell line xenograft models, suppression of tumor growth was observed in the antibody administration group. These results suggested that the TfR006 antibody should have a strong growth-suppressing effect on various types of cancer cells.

Example 8

Antitumor Effects of Anti-TfR Antibody on ATL Models

The ATL cell line MT-2 was cultured in an RPMI 1640 culture medium supplemented with 10% FBS. Upon transplantation, the cells were recovered by centrifugation, and were then suspended in RPMI1640 to a cell density of 1×10$^8$ cells/mL. This cell suspension was mixed with the same amount of Matrigel (Becton, Dickinson and Company), and the obtained mixture was then transplanted into the subcutis on the right abdomen of each NOG/Jic mouse (female, 7-week-old, Central Institute for Experimental Animals). After completion of the transplantation, the tumor diameter of each mouse was measured with a vernier caliper twice a week. At the time point at which the mean tumor volume reached approximately 150 mm$^3$, the mice were divided into four groups (five mice per group) according to random assignment regarding tumor volume. To the three groups, the TfR 006 antibody was administered into the caudal vein of each mouse at doses of 15 mg/kg group, 5 mg/kg group, and 1.5 mg/kg group. To the remaining one group used as a negative control, PBS was administered at an amount of 0.2 mL/20 g mouse into the caudal vein of each mouse. Administration was carried out twice a week (every three or four days) in a total of six times. Even after completion of the administration, the tumor diameter was measured with a vernier caliper twice a week, as with before the assignment, so that the tumor volumes in each group were obtained. Antitumor effects were determined based on the tumor volumes on the final day of measurement according to a parametric Dunnet's multiple comparison test using the PBS group as a control.

Tumor volume was calculated according to the following formula.

Tumor volume=(Minor axis)$^2$×Major axis×0.5

The random assignment and the multiple comparison test were performed using animal experiment data statistical analysis software EXSUS (CLC Corporation).

Figure 5:
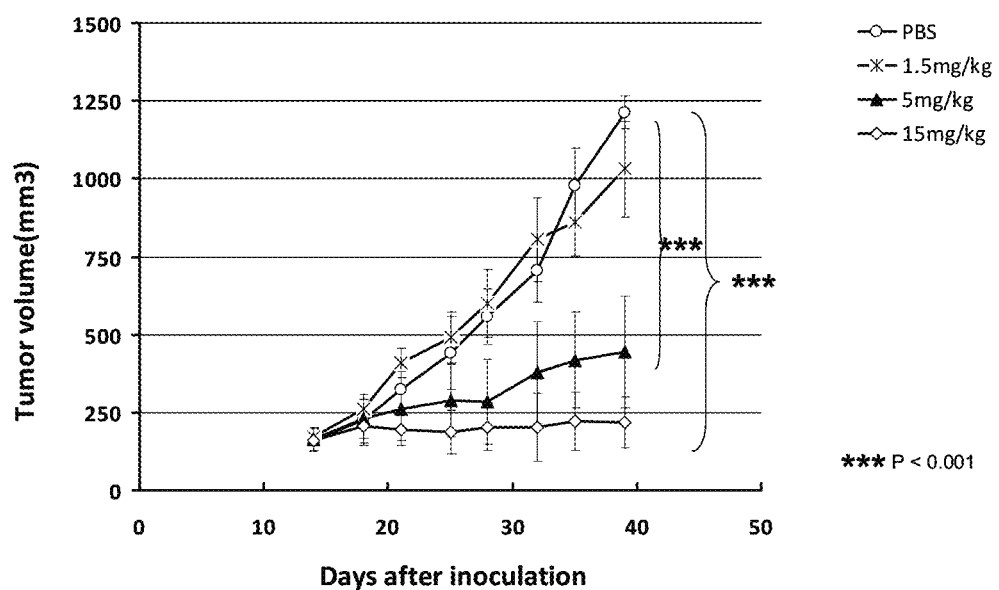
FIG. 5 shows the antitumor effects of the TfR006 IgG antibody on ATL models.

A change over time in a mean value of the tumor volumes in each group is shown in FIG. 5. As shown in FIG. 5, the growth of a tumor was dose-dependently suppressed by the TfR006 antibody.

Example 9

Immunostaining Using Clinical Analytes (1) Preparation of Sections

The excised lung cancer tissues were cut into a size of approximately 5 mm×5 mm×10 mm, and the obtained section was added into a 4% PFA/0.01% glutaraldehyde/0.1 M cacodylic acid buffer at 4° C. (wherein PFA was manufactured by Wako Pure Chemical Industries, Ltd.; glutaraldehyde was manufactured by Kanto Chemical Co, Inc.; and sodium cacodylate was manufactured by SIGMA), and it was then immobilized by microwave radiation using a microwave oven (SHARP). Thereafter, it was immobilized again with the same immobilization solution at 4° C. for 1 hour. Thereafter, the resultant was transferred into 10% sucrose/PBS, and was then immersed therein at 4° C. for 4 hours. Subsequently, the 10% sucrose/PBS was replaced with 15% sucrose/PBS, and the product was then immersed therein at 4° C. for 4 hours. Then, the 15% sucrose/PBS was replaced with 20% sucrose/PBS, and the product was further immersed therein at 4° C. overnight. The resultant was embedded in OTC compound, and was then rapidly frozen in dry ice/hexane. The resultant was sliced into a section with a thickness of 4 μm in a cryostat (Reichert-Jung 2800 FRIGCUT E), and the obtained section was then attached onto a silane-coated slide glass (MATSUNAMI), followed by air-drying with a cold air dryer for 30 minutes.

(2) Staining

Figure 6:
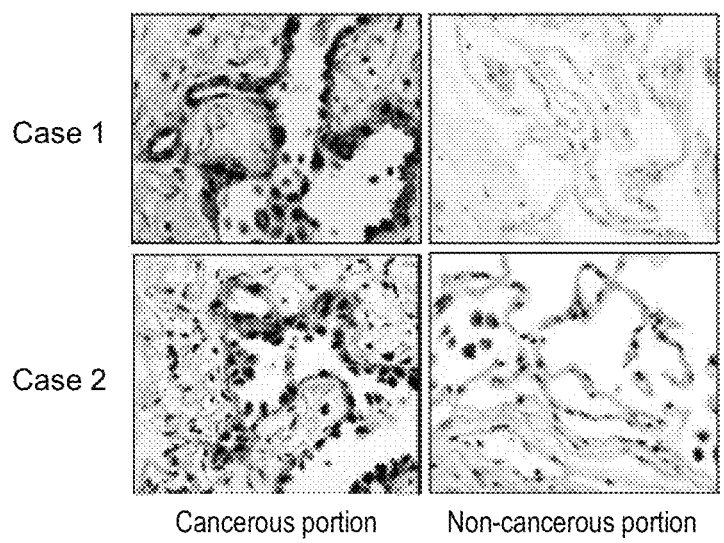
FIG. 6 shows the reactivity of clinically-derived lung tissue samples with the TfR006 phage antibody.

The section-attached slide glass was immersed in PBS three times for 5 minutes for each immersion to achieve hydrophilicity. Subsequently, 50 μL of 0.3% $H_2O_2$/0.1% $NaN_3$ was added dropwise to the resulting slide glass, and they were then reacted at room temperature for 10 minutes so as to block endogenous peroxidase. Thereafter, the slide glass was washed with PBS three times for 5 minutes for each washing, and it was then placed in 2% BSA2/PBS to block a non-specific reaction at room temperature for 10 minutes. Excessive liquid was discarded, and the phage antibody TfR006 (50 μL) was added dropwise thereto, followed by performing a reaction at room temperature for 1 hour. Thereafter, the product was washed with PBS three times, and 50 μL of 5 μg/mL anti-cp3 rabbit antibody was then added dropwise thereto, followed by performing a reaction with a secondary antibody at room temperature for 45 minutes. Thereafter, the product was washed with PBS three times, and 50 μL of peroxidase labeled dextran-binding anti-rabbit immunoglobulin-goat polyclonal antibody (DAKO) was then added dropwise thereto, followed by performing a reaction with tertiary antibody at room temperature for 30 minutes. Thereafter, the product was washed with PBS three times, and 50 μL of DAB.$H_2O_2$ coloring solution was added dropwise thereto to develop a brown color. Then, the reaction product was transferred into a vat filled with distilled water, so as to terminate the reaction. Thereafter, the product was washed with water for 10 minutes, and nuclear staining with hematoxylin, dehydration and penetration were carried out. The resultant was mounted with Malinol and was then observed under a microscope. As shown in FIG. 6, the present antibody reacts with cancer cells of lung cancer, but does not react with non-cancer cells.

The invention claimed is:

1. An antibody which specifically reacts with human transferrin receptor (TfR), wherein said antibody inhibits cell growth on TfR-expressing tumor cells, and wherein said antibody comprises a heavy chain variable region having CDR consisting of the heavy chain first complementarity determining region (VH CDR1) of SEQ ID NO: 31, the heavy chain second complementarity determining region (VH CDR2) of SEQ ID NO: 32, and the heavy chain third complementarity determining region (VH CDR3) of SEQ ID NO: 33, and a light chain variable region having CDR consisting of the light chain first complementarity determining region (VL CDR1) of SEQ ID NO: 34, the light chain second complementarity determining region (VL CDR2) of SEQ ID NO: 35, and the light chain third complementarity determining region (VL CDR3) of SEQ ID NO: 36.

2. The antibody according to claim 1, which is a human antibody or a humanized antibody.

3. The antibody according to claim 1, which is an antibody fragment selected from the group consisting of Fab, Fab', F(ab')$_2$, a single-chain antibody (scFv), a dimerized V region (Diabody).

4. A method for producing the antibody according to claim 1, which comprises culturing a transformed cell line which is obtained by introducing a recombinant vector into a host cell, said recombinant vector comprises DNA which encodes said antibody in a medium, generating and accumulating the antibody in the culture, and then collecting the antibody from the culture.

5. A pharmaceutical composition which comprises the antibody according to claim 1.

6. The pharmaceutical composition according to claim 5, wherein a cytotoxic substance is bound to the antibody.

7. The pharmaceutical composition according to claim 6, wherein the cytotoxic substance is a drug, a toxin, or a radioactive substance.

8. The pharmaceutical composition according to claim 5, which is used as an anticancer agent.

9. The pharmaceutical composition according to claim 8, wherein the cancer is a solid cancer or a blood cancer.

10. The pharmaceutical composition according to claim 8, wherein the solid cancer is lung cancer, colon cancer, stomach cancer, bladder cancer, pancreatic cancer, prostate cancer, hepatic cancer, cervical cancer, uterine cancer, ovarian cancer, breast cancer, head and neck cancer, or skin cancer.

11. The pharmaceutical composition according to claim 8, wherein the blood cancer is leukemia, lymphoma, or myeloma.

12. The pharmaceutical composition according to claim 8, wherein the blood cancer is adult T-cell leukemia (ATL).

13. An antibody which specifically reacts with human transferrin receptor (TfR), wherein said antibody inhibits cell growth on TfR-expressing tumor cells, and wherein said antibody comprises a heavy chain variable region having CDR consisting of the heavy chain first complementarity determining region (VH CDR1) of SEQ ID NO: 97, the heavy chain second complementarity determining region (VH CDR2) of SEQ ID NO: 98, and the heavy chain third complementarity determining region (VH CDR3) of SEQ ID NO: 99, and a light chain variable region having CDR consisting of the light chain first complementarity determining region (VL CDR1) of SEQ ID NO: 100, the light chain second complementarity determining region (VL CDR2) of SEQ ID NO: 101, and the light chain third complementarity determining region (VL CDR3) of SEQ ID NO: 102.

14. An antibody which specifically reacts with human transferrin receptor (TfR), wherein said antibody inhibits cell growth on TfR-expressing tumor cells, and wherein said antibody comprises a heavy chain variable region having CDR consisting of the heavy chain first complementarity determining region (VH CDR1) of SEQ ID NO: 115, the heavy chain second complementarity determining region (VH CDR2) of SEQ ID NO: 116, and the heavy chain third complementarity determining region (VH CDR3) of SEQ ID NO: 117, and a light chain variable region having CDR consisting of the light chain first complementarity determining region (VL CDR1) of SEQ ID NO: 118, the light chain second complementarity determining region (VL CDR2) of SEQ ID NO: 119, and the light chain third complementarity determining region (VL CDR3) of SEQ ID NO: 120.

15. The antibody according to claim 13, which is a human antibody or a humanized antibody.

16. The antibody according to claim 13, which is an antibody fragment selected from the group consisting of Fab, Fab', F(ab')$_2$, a single-chain antibody (scFv), a dimerized V region (Diabody).

17. A method for producing the antibody according to claim 13, which comprises culturing a transformed cell line which is obtained by introducing a recombinant vector into a host cell, said recombinant vector comprises DNA which encodes said antibody in a medium, generating and accumulating the antibody in the culture, and then collecting the antibody from the culture.

18. A pharmaceutical composition which comprises the antibody according to claim 13.

19. The pharmaceutical composition according to claim 18, wherein a cytotoxic substance is bound to the antibody.

20. The pharmaceutical composition according to claim 19, wherein the cytotoxic substance is a drug, a toxin, or a radioactive substance.

21. The pharmaceutical composition according to claim 18, which is used as an anticancer agent.

22. The pharmaceutical composition according to claim 21, wherein the cancer is a solid cancer or a blood cancer.

23. The pharmaceutical composition according to claim 21, wherein the solid cancer is lung cancer, colon cancer, stomach cancer, bladder cancer, pancreatic cancer, prostate cancer, hepatic cancer, cervical cancer, uterine cancer, ovarian cancer, breast cancer, head and neck cancer, or skin cancer.

24. The pharmaceutical composition according to claim 21, wherein the blood cancer is leukemia, lymphoma, or myeloma.

25. The pharmaceutical composition according to claim 21, wherein the blood cancer is adult T-cell leukemia (ATL).

26. The antibody according to claim 14, which is a human antibody or a humanized antibody.

27. The antibody according to claim 14, which is an antibody fragment selected from the group consisting of Fab, Fab', F(ab')$_2$, a single-chain antibody (scFv), a dimerized V region (Diabody).

28. A method for producing the antibody according to claim 14, which comprises culturing a transformed cell line which is obtained by introducing a recombinant vector into a host cell, said recombinant vector comprises DNA which encodes said antibody in a medium, generating and accumulating the antibody in the culture, and then collecting the antibody from the culture.

29. A pharmaceutical composition which comprises the antibody according to claim 14.

30. The pharmaceutical composition according to claim 29, wherein a cytotoxic substance is bound to the antibody.

31. The pharmaceutical composition according to claim 30, wherein the cytotoxic substance is a drug, a toxin, or a radioactive substance.

32. The pharmaceutical composition according to claim 29, which is used as an anticancer agent.

33. The pharmaceutical composition according to claim 32, wherein the cancer is a solid cancer or a blood cancer.

34. The pharmaceutical composition according to claim 32, wherein the solid cancer is lung cancer, colon cancer, stomach cancer, bladder cancer, pancreatic cancer, prostate cancer, hepatic cancer, cervical cancer, uterine cancer, ovarian cancer, breast cancer, head and neck cancer, or skin cancer.

35. The pharmaceutical composition according to claim 32, wherein the blood cancer is leukemia, lymphoma, or myeloma.

36. The pharmaceutical composition according to claim 32, wherein the blood cancer is adult T-cell leukemia (ATL).

* * * * *

SEQUENCE LISTING

<160> NUMBER OF SEQ ID NOS: 125

<210> SEQ ID NO 1
<211> LENGTH: 7
<212> TYPE: PRT
<213> ORGANISM: human

<400> SEQUENCE: 1

Thr Ser Gly Val Gly Val Gly
1               5

<210> SEQ ID NO 2
<211> LENGTH: 16
<212> TYPE: PRT
<213> ORGANISM: human

<400> SEQUENCE: 2

Leu Ile Tyr Trp Asp Asp Asp Lys His Tyr Ser Pro Ser Leu Lys Ser
1               5                   10                  15

<210> SEQ ID NO 3
<211> LENGTH: 10
<212> TYPE: PRT
<213> ORGANISM: human

<400> SEQUENCE: 3

Asn Gly Asp Tyr Gly Ile Glu Phe Asp Tyr
1               5                   10

<210> SEQ ID NO 4
<211> LENGTH: 11
<212> TYPE: PRT
<213> ORGANISM: human

<400> SEQUENCE: 4

Gly Gly Asn Asn Ile Gly Ser Lys Ser Val His
1               5                   10

<210> SEQ ID NO 5
<211> LENGTH: 7
<212> TYPE: PRT
<213> ORGANISM: human

<400> SEQUENCE: 5

Tyr Asp Ser Asp Arg Pro Ser
1               5

<210> SEQ ID NO 6
<211> LENGTH: 11
<212> TYPE: PRT
<213> ORGANISM: human

<400> SEQUENCE: 6

Gln Val Trp Asp Ser Ser Asp His Val Val
1               5                   10

<210> SEQ ID NO 7
<211> LENGTH: 5
<212> TYPE: PRT
<213> ORGANISM: human

<400> SEQUENCE: 7

Ser Tyr Ser Met Asn
1               5

```
<210> SEQ ID NO 8
<211> LENGTH: 17
<212> TYPE: PRT
<213> ORGANISM: human

<400> SEQUENCE: 8

Ser Ile Ser Ser Ser Ser Ser Tyr Ile Tyr Tyr Ala Asp Ser Val Lys
1               5                   10                  15
Gly

<210> SEQ ID NO 9
<211> LENGTH: 10
<212> TYPE: PRT
<213> ORGANISM: human

<400> SEQUENCE: 9

Ala Arg Glu Ser Val Asp Ala Phe Asp Ile
1               5                   10

<210> SEQ ID NO 10
<211> LENGTH: 11
<212> TYPE: PRT
<213> ORGANISM: human

<400> SEQUENCE: 10

Gln Gly Asp Ser Leu Arg Ser Tyr Asp Ala Ser
1               5                   10

<210> SEQ ID NO 11
<211> LENGTH: 7
<212> TYPE: PRT
<213> ORGANISM: human

<400> SEQUENCE: 11

Gly Leu Ser Asp Arg Pro Ser
1               5

<210> SEQ ID NO 12
<211> LENGTH: 10
<212> TYPE: PRT
<213> ORGANISM: human

<400> SEQUENCE: 12

Ile Ser Arg Asp Ser Gly Gly Asn Pro His
1               5                   10

<210> SEQ ID NO 13
<211> LENGTH: 5
<212> TYPE: PRT
<213> ORGANISM: human

<400> SEQUENCE: 13

Ser Tyr Ala Met Ser
1               5

<210> SEQ ID NO 14
<211> LENGTH: 17
<212> TYPE: PRT
<213> ORGANISM: human

<400> SEQUENCE: 14

Ala Ile Ser Gly Ser Gly Gly Ser Thr Tyr Tyr Ala Asp Ser Val Lys
1               5                   10                  15
Gly
```

-continued

```
<210> SEQ ID NO 15
<211> LENGTH: 13
<212> TYPE: PRT
<213> ORGANISM: human

<400> SEQUENCE: 15

Gly Tyr Tyr Gly Ser Asn Tyr Tyr Tyr Gly Met Asp Val
1               5                   10

<210> SEQ ID NO 16
<211> LENGTH: 13
<212> TYPE: PRT
<213> ORGANISM: human

<400> SEQUENCE: 16

Ser Gly Ser Ser Ser Asn Ile Gly Ser Asn Tyr Val Tyr
1               5                   10

<210> SEQ ID NO 17
<211> LENGTH: 7
<212> TYPE: PRT
<213> ORGANISM: human

<400> SEQUENCE: 17

Arg Asn Asn Gln Arg Pro Ser
1               5

<210> SEQ ID NO 18
<211> LENGTH: 11
<212> TYPE: PRT
<213> ORGANISM: human

<400> SEQUENCE: 18

Ala Ala Trp Asp Asp Ser Leu Ser Gly Pro Val
1               5                   10

<210> SEQ ID NO 19
<211> LENGTH: 5
<212> TYPE: PRT
<213> ORGANISM: human

<400> SEQUENCE: 19

Asp Phe Val Phe Ser
1               5

<210> SEQ ID NO 20
<211> LENGTH: 17
<212> TYPE: PRT
<213> ORGANISM: human

<400> SEQUENCE: 20

Trp Ile Ser Ala His Asp Gly Asn Thr Asn Tyr Ala Gln Lys Leu Gln
1               5                   10                  15

Asp

<210> SEQ ID NO 21
<211> LENGTH: 17
<212> TYPE: PRT
<213> ORGANISM: human

<400> SEQUENCE: 21

Asp Thr Phe Thr Asn Leu Leu Gly Asp Tyr Ser Tyr Asp Ala Met Asp
1               5                   10                  15

Val
```

```
<210> SEQ ID NO 22
<211> LENGTH: 14
<212> TYPE: PRT
<213> ORGANISM: human

<400> SEQUENCE: 22

Gly Ser Ser Thr Gly Ala Val Thr Ser Gly His Tyr Pro Tyr
1               5                   10

<210> SEQ ID NO 23
<211> LENGTH: 7
<212> TYPE: PRT
<213> ORGANISM: human

<400> SEQUENCE: 23

Asp Thr Thr Glu Lys His Ser
1               5

<210> SEQ ID NO 24
<211> LENGTH: 10
<212> TYPE: PRT
<213> ORGANISM: human

<400> SEQUENCE: 24

Leu Leu Ser Ser Gly Asp Gly Arg Ala Val
1               5                   10

<210> SEQ ID NO 25
<211> LENGTH: 5
<212> TYPE: PRT
<213> ORGANISM: human

<400> SEQUENCE: 25

Asn Tyr Gly Met Ser
1               5

<210> SEQ ID NO 26
<211> LENGTH: 17
<212> TYPE: PRT
<213> ORGANISM: human

<400> SEQUENCE: 26

Trp Ile Ser Ala Tyr Asn Gly Asn Thr Asn Tyr Gly Glu Lys Leu Gln
1               5                   10                  15

Gly

<210> SEQ ID NO 27
<211> LENGTH: 13
<212> TYPE: PRT
<213> ORGANISM: human

<400> SEQUENCE: 27

Asp Asp Tyr Tyr Gly Ser Gly Val Asp Ala Phe Asp Ile
1               5                   10

<210> SEQ ID NO 28
<211> LENGTH: 11
<212> TYPE: PRT
<213> ORGANISM: human

<400> SEQUENCE: 28

Gly Gly Asn Lys Ile Gly Ser Lys Ser Val His
1               5                   10
```

```
<210> SEQ ID NO 29
<211> LENGTH: 7
<212> TYPE: PRT
<213> ORGANISM: human

<400> SEQUENCE: 29

Tyr Asp Arg Asp Arg Pro Ser
1               5

<210> SEQ ID NO 30
<211> LENGTH: 10
<212> TYPE: PRT
<213> ORGANISM: human

<400> SEQUENCE: 30

Gln Val Trp Asp Ser Ser Ser Asp Val Val
1               5                   10

<210> SEQ ID NO 31
<211> LENGTH: 5
<212> TYPE: PRT
<213> ORGANISM: human

<400> SEQUENCE: 31

Ser Tyr Gly Met His
1               5

<210> SEQ ID NO 32
<211> LENGTH: 17
<212> TYPE: PRT
<213> ORGANISM: human

<400> SEQUENCE: 32

Val Ile Ser Phe Asp Gly Ser Ser Lys Tyr Tyr Ala Asp Ser Val Lys
1               5                   10                  15

Gly

<210> SEQ ID NO 33
<211> LENGTH: 14
<212> TYPE: PRT
<213> ORGANISM: human

<400> SEQUENCE: 33

Asp Ser Asn Phe Trp Ser Gly Tyr Tyr Ser Pro Val Asp Val
1               5                   10

<210> SEQ ID NO 34
<211> LENGTH: 13
<212> TYPE: PRT
<213> ORGANISM: human

<400> SEQUENCE: 34

Thr Arg Ser Ser Gly Ser Ile Ala Ser Asn Ser Val Gln
1               5                   10

<210> SEQ ID NO 35
<211> LENGTH: 8
<212> TYPE: PRT
<213> ORGANISM: human

<400> SEQUENCE: 35

Tyr Glu Asp Thr Gln Arg Pro Ser
1               5
```

```
<210> SEQ ID NO 36
<211> LENGTH: 10
<212> TYPE: PRT
<213> ORGANISM: human

<400> SEQUENCE: 36

Gln Ser Tyr Asp Ser Ala Tyr His Trp Val
1               5                   10

<210> SEQ ID NO 37
<211> LENGTH: 5
<212> TYPE: PRT
<213> ORGANISM: human

<400> SEQUENCE: 37

Ser Tyr Trp Leu Ser
1               5

<210> SEQ ID NO 38
<211> LENGTH: 17
<212> TYPE: PRT
<213> ORGANISM: human

<400> SEQUENCE: 38

Lys Ile Asp Pro Ser Asp Ser Tyr Thr Gln Tyr Ser Pro Ser Phe Glu
1               5                   10                  15

Gly

<210> SEQ ID NO 39
<211> LENGTH: 8
<212> TYPE: PRT
<213> ORGANISM: human

<400> SEQUENCE: 39

His Gly Tyr Asp Ala Phe His Val
1               5

<210> SEQ ID NO 40
<211> LENGTH: 13
<212> TYPE: PRT
<213> ORGANISM: human

<400> SEQUENCE: 40

Ser Gly Ser Ser Ser Asn Ile Gly Asn Asn Ala Val Asn
1               5                   10

<210> SEQ ID NO 41
<211> LENGTH: 7
<212> TYPE: PRT
<213> ORGANISM: human

<400> SEQUENCE: 41

Tyr Asp Asp Leu Leu Pro Ser
1               5

<210> SEQ ID NO 42
<211> LENGTH: 11
<212> TYPE: PRT
<213> ORGANISM: human

<400> SEQUENCE: 42

Ala Ala Trp Asp Asp Ser Leu Asn Gly Trp Val
1               5                   10
```

<210> SEQ ID NO 43
<211> LENGTH: 5
<212> TYPE: PRT
<213> ORGANISM: human

<400> SEQUENCE: 43

Asp Tyr Ala Met His
1               5

<210> SEQ ID NO 44
<211> LENGTH: 17
<212> TYPE: PRT
<213> ORGANISM: human

<400> SEQUENCE: 44

Gly Ile Ser Trp Asn Ser Gly Ser Ile Gly Tyr Ala Asp Ser Val Lys
1               5                   10                  15

Gly

<210> SEQ ID NO 45
<211> LENGTH: 13
<212> TYPE: PRT
<213> ORGANISM: human

<400> SEQUENCE: 45

Asp Gln His Arg Glu Phe Tyr Tyr Tyr Gly Met Asp Val
1               5                   10

<210> SEQ ID NO 46
<211> LENGTH: 13
<212> TYPE: PRT
<213> ORGANISM: human

<400> SEQUENCE: 46

Ser Gly Ser Ser Ser Asn Ile Gly Ser Asn Tyr Val Tyr
1               5                   10

<210> SEQ ID NO 47
<211> LENGTH: 7
<212> TYPE: PRT
<213> ORGANISM: human

<400> SEQUENCE: 47

Arg Asn Asn Gln Arg Pro Ser
1               5

<210> SEQ ID NO 48
<211> LENGTH: 11
<212> TYPE: PRT
<213> ORGANISM: human

<400> SEQUENCE: 48

Ala Ala Trp Asp Asp Ser Leu Ser Gly Pro Val
1               5                   10

<210> SEQ ID NO 49
<211> LENGTH: 5
<212> TYPE: PRT
<213> ORGANISM: human

<400> SEQUENCE: 49

Ser Tyr Trp Ile Gly
1               5

-continued

```
<210> SEQ ID NO 50
<211> LENGTH: 17
<212> TYPE: PRT
<213> ORGANISM: human

<400> SEQUENCE: 50

Ile Ile Tyr Pro Gly Asp Ser Asp Thr Arg Tyr Ser Pro Ser Phe Gln
1               5                   10                  15

Gly

<210> SEQ ID NO 51
<211> LENGTH: 13
<212> TYPE: PRT
<213> ORGANISM: human

<400> SEQUENCE: 51

Gln Gly Thr Asn Trp Gly Val Gly Asp Ala Phe Asp Ile
1               5                   10

<210> SEQ ID NO 52
<211> LENGTH: 11
<212> TYPE: PRT
<213> ORGANISM: human

<400> SEQUENCE: 52

Gly Gly Asn Asn Ile Gly Ser Lys Ser Val His
1               5                   10

<210> SEQ ID NO 53
<211> LENGTH: 7
<212> TYPE: PRT
<213> ORGANISM: human

<400> SEQUENCE: 53

Asp Asp Ser Asp Arg Pro Ser
1               5

<210> SEQ ID NO 54
<211> LENGTH: 11
<212> TYPE: PRT
<213> ORGANISM: human

<400> SEQUENCE: 54

Gln Val Trp Asp Ile Ser Ser Asp His Val Val
1               5                   10

<210> SEQ ID NO 55
<211> LENGTH: 5
<212> TYPE: PRT
<213> ORGANISM: human

<400> SEQUENCE: 55

Ser Tyr Ala Met Ser
1               5

<210> SEQ ID NO 56
<211> LENGTH: 17
<212> TYPE: PRT
<213> ORGANISM: human

<400> SEQUENCE: 56

Ala Ile Ser Gly Ser Gly Gly Ser Thr Tyr Tyr Ala Asp Ser Val Lys
1               5                   10                  15

Gly
```

```
<210> SEQ ID NO 57
<211> LENGTH: 16
<212> TYPE: PRT
<213> ORGANISM: human

<400> SEQUENCE: 57

Asp Arg Tyr Tyr Tyr Gly Ser Gly Ser Tyr Tyr Asp Ala Phe Asp Ile
1               5                   10                  15

<210> SEQ ID NO 58
<211> LENGTH: 11
<212> TYPE: PRT
<213> ORGANISM: human

<400> SEQUENCE: 58

Gln Gly Asp Ser Leu Arg Ser Tyr Tyr Ala Ser
1               5                   10

<210> SEQ ID NO 59
<211> LENGTH: 7
<212> TYPE: PRT
<213> ORGANISM: human

<400> SEQUENCE: 59

Gly Lys Asn Asn Arg Pro Ser
1               5

<210> SEQ ID NO 60
<211> LENGTH: 11
<212> TYPE: PRT
<213> ORGANISM: human

<400> SEQUENCE: 60

Asn Ser Arg Asp Ser Ser Gly Asn His Val Val
1               5                   10

<210> SEQ ID NO 61
<211> LENGTH: 5
<212> TYPE: PRT
<213> ORGANISM: human

<400> SEQUENCE: 61

Ser Tyr Ser Met Asn
1               5

<210> SEQ ID NO 62
<211> LENGTH: 17
<212> TYPE: PRT
<213> ORGANISM: human

<400> SEQUENCE: 62

Val Ile Ser Tyr Asp Gly Ser Asn Lys Tyr Tyr Ala Asp Ser Val Lys
1               5                   10                  15

Gly

<210> SEQ ID NO 63
<211> LENGTH: 12
<212> TYPE: PRT
<213> ORGANISM: human

<400> SEQUENCE: 63

Val Asp Pro Gly Asp Arg Gly Trp Tyr Phe Asp Leu
1               5                   10
```

```
<210> SEQ ID NO 64
<211> LENGTH: 13
<212> TYPE: PRT
<213> ORGANISM: human

<400> SEQUENCE: 64

Ser Gly Ser Ser Ser Asn Ile Gly Ser Asn Thr Val Asn
1               5                   10

<210> SEQ ID NO 65
<211> LENGTH: 7
<212> TYPE: PRT
<213> ORGANISM: 65

<400> SEQUENCE: 65

Ser Asn Asn Gln Arg Pro Ser
1               5

<210> SEQ ID NO 66
<211> LENGTH: 11
<212> TYPE: PRT
<213> ORGANISM: human

<400> SEQUENCE: 66

Ala Ala Trp Asp Asp Ser Leu Asn Gly Trp Val
1               5                   10

<210> SEQ ID NO 67
<211> LENGTH: 7
<212> TYPE: PRT
<213> ORGANISM: human

<400> SEQUENCE: 67

Ser Ser Pro Tyr Tyr Trp Gly
1               5

<210> SEQ ID NO 68
<211> LENGTH: 16
<212> TYPE: PRT
<213> ORGANISM: human

<400> SEQUENCE: 68

Ser Val Tyr Tyr Ser Gly Asn Thr Tyr Tyr Asn Pro Ser Leu Thr Arg
1               5                   10                  15

<210> SEQ ID NO 69
<211> LENGTH: 11
<212> TYPE: PRT
<213> ORGANISM: human

<400> SEQUENCE: 69

His Ser Trp Gly Ile Asn Asp Ala Phe Asp Val
1               5                   10

<210> SEQ ID NO 70
<211> LENGTH: 13
<212> TYPE: PRT
<213> ORGANISM: human

<400> SEQUENCE: 70

Ser Gly Ser Ser Ser Asn Ile Gly Asn Asn Tyr Val Ser
1               5                   10
```

```
<210> SEQ ID NO 71
<211> LENGTH: 7
<212> TYPE: PRT
<213> ORGANISM: human

<400> SEQUENCE: 71

Asp Asn Asn Lys Arg Pro Ser
1               5

<210> SEQ ID NO 72
<211> LENGTH: 11
<212> TYPE: PRT
<213> ORGANISM: human

<400> SEQUENCE: 72

Gly Thr Trp Asp Ser Ser Leu Ser Val Trp Val
1               5                   10

<210> SEQ ID NO 73
<211> LENGTH: 5
<212> TYPE: PRT
<213> ORGANISM: human

<400> SEQUENCE: 73

Asp Tyr Ala Met His
1               5

<210> SEQ ID NO 74
<211> LENGTH: 17
<212> TYPE: PRT
<213> ORGANISM: human

<400> SEQUENCE: 74

Gly Ile Ser Trp Asn Ser Gly Ser Ile Asp Tyr Ala Asp Ser Val Lys
1               5                   10                  15

Gly

<210> SEQ ID NO 75
<211> LENGTH: 10
<212> TYPE: PRT
<213> ORGANISM: human

<400> SEQUENCE: 75

Glu Asn Leu Ala Val Ala Gly Leu Asp Tyr
1               5                   10

<210> SEQ ID NO 76
<211> LENGTH: 11
<212> TYPE: PRT
<213> ORGANISM: human

<400> SEQUENCE: 76

Gln Gly Asp Ser Leu Arg Gly Tyr Tyr Ala Ser
1               5                   10

<210> SEQ ID NO 77
<211> LENGTH: 7
<212> TYPE: PRT
<213> ORGANISM: human

<400> SEQUENCE: 77

Asp Lys Asn Thr Arg Pro Ser
1               5
```

```
<210> SEQ ID NO 78
<211> LENGTH: 11
<212> TYPE: PRT
<213> ORGANISM: human

<400> SEQUENCE: 78

Gln Ser Arg Asp Asn Ser Gly Glu Met Val Val
1               5                   10

<210> SEQ ID NO 79
<211> LENGTH: 5
<212> TYPE: PRT
<213> ORGANISM: human

<400> SEQUENCE: 79

Glu Leu Ser Met His
1               5

<210> SEQ ID NO 80
<211> LENGTH: 17
<212> TYPE: PRT
<213> ORGANISM: human

<400> SEQUENCE: 80

Gly Phe Asp Pro Glu Asp Gly Glu Thr Ile Tyr Ala Gln Lys Phe Gln
1               5                   10                  15

Gly

<210> SEQ ID NO 81
<211> LENGTH: 15
<212> TYPE: PRT
<213> ORGANISM: human

<400> SEQUENCE: 81

Asp Ala Tyr Tyr Gly Ser Gly Ser Pro Arg Asp Ala Phe Asp Ile
1               5                   10                  15

<210> SEQ ID NO 82
<211> LENGTH: 11
<212> TYPE: PRT
<213> ORGANISM: human

<400> SEQUENCE: 82

Gly Gly Asp Asn Val Gly Gly Lys Ser Leu His
1               5                   10

<210> SEQ ID NO 83
<211> LENGTH: 7
<212> TYPE: PRT
<213> ORGANISM: human

<400> SEQUENCE: 83

Asp Asp Arg Asp Arg Pro Ser
1               5

<210> SEQ ID NO 84
<211> LENGTH: 11
<212> TYPE: PRT
<213> ORGANISM: human

<400> SEQUENCE: 84

Gln Val Trp Asp Asp Ile Ser Arg Leu Val Ile
1               5                   10
```

```
<210> SEQ ID NO 85
<211> LENGTH: 5
<212> TYPE: PRT
<213> ORGANISM: human

<400> SEQUENCE: 85

Ser Tyr Tyr Ile His
1               5

<210> SEQ ID NO 86
<211> LENGTH: 17
<212> TYPE: PRT
<213> ORGANISM: human

<400> SEQUENCE: 86

Ile Ile Asn Pro Arg Gly Gly Thr Asp Phe Ala Gln Lys Phe Gln
1               5                   10                  15

Gly

<210> SEQ ID NO 87
<211> LENGTH: 15
<212> TYPE: PRT
<213> ORGANISM: human

<400> SEQUENCE: 87

Gly Asp Cys Thr Asn Gly Val Cys Tyr Ser Gly Gly Leu Asp Val
1               5                   10                  15

<210> SEQ ID NO 88
<211> LENGTH: 13
<212> TYPE: PRT
<213> ORGANISM: human

<400> SEQUENCE: 88

Ser Gly Ser Ser Ser Asn Ile Gly Asn Asn Tyr Val Ser
1               5                   10

<210> SEQ ID NO 89
<211> LENGTH: 7
<212> TYPE: PRT
<213> ORGANISM: human

<400> SEQUENCE: 89

Asp Asn Asp Lys Arg Pro Ser
1               5

<210> SEQ ID NO 90
<211> LENGTH: 10
<212> TYPE: PRT
<213> ORGANISM: human

<400> SEQUENCE: 90

Gly Thr Trp Asp Asn Ser Leu Ser Gly Val
1               5                   10

<210> SEQ ID NO 91
<211> LENGTH: 5
<212> TYPE: PRT
<213> ORGANISM: human

<400> SEQUENCE: 91

Asp Tyr Ala Met His
1               5
```

```
<210> SEQ ID NO 92
<211> LENGTH: 17
<212> TYPE: PRT
<213> ORGANISM: human

<400> SEQUENCE: 92

Gly Ile Ser Trp Asn Ser Gly Ser Ile Gly Tyr Ala Asp Ser Val Lys
1               5                   10                  15

Gly

<210> SEQ ID NO 93
<211> LENGTH: 13
<212> TYPE: PRT
<213> ORGANISM: human

<400> SEQUENCE: 93

Asp Val Asp Leu Trp Phe Gly Glu Tyr Tyr Phe Asp Tyr
1               5                   10

<210> SEQ ID NO 94
<211> LENGTH: 13
<212> TYPE: PRT
<213> ORGANISM: human

<400> SEQUENCE: 94

Ser Gly Ser Ser Ser Asn Ile Gly Asn Asn Tyr Val Ser
1               5                   10

<210> SEQ ID NO 95
<211> LENGTH: 7
<212> TYPE: PRT
<213> ORGANISM: human

<400> SEQUENCE: 95

Asp Asn Asn Lys Arg Pro Ser
1               5

<210> SEQ ID NO 96
<211> LENGTH: 12
<212> TYPE: PRT
<213> ORGANISM: human

<400> SEQUENCE: 96

Gly Thr Trp Asp Ser Ser Leu Ser Ala Pro Tyr Val
1               5                   10

<210> SEQ ID NO 97
<211> LENGTH: 5
<212> TYPE: PRT
<213> ORGANISM: human

<400> SEQUENCE: 97

Asp Tyr Ala Met Tyr
1               5

<210> SEQ ID NO 98
<211> LENGTH: 17
<212> TYPE: PRT
<213> ORGANISM: human

<400> SEQUENCE: 98

Gly Ile Asn Trp Asn Ser Ala Ile Ile Gly Tyr Ala Asp Ser Val Lys
1               5                   10                  15

Gly
```

<210> SEQ ID NO 99
<211> LENGTH: 11
<212> TYPE: PRT
<213> ORGANISM: human

<400> SEQUENCE: 99

Glu Ala Leu Tyr Tyr Ser Ala Phe Phe Asp Ser
1               5                   10

<210> SEQ ID NO 100
<211> LENGTH: 13
<212> TYPE: PRT
<213> ORGANISM: human

<400> SEQUENCE: 100

Ser Gly Ser Ser Ser Asn Ile Gly Asn Asn Tyr Val Ser
1               5                   10

<210> SEQ ID NO 101
<211> LENGTH: 7
<212> TYPE: PRT
<213> ORGANISM: human

<400> SEQUENCE: 101

Asp Asn Asn Lys Arg Pro Ser
1               5

<210> SEQ ID NO 102
<211> LENGTH: 11
<212> TYPE: PRT
<213> ORGANISM: human

<400> SEQUENCE: 102

Gly Thr Trp Asp Ser Ser Leu Ser Ala Trp Val
1               5                   10

<210> SEQ ID NO 103
<211> LENGTH: 5
<212> TYPE: PRT
<213> ORGANISM: human

<400> SEQUENCE: 103

Asp Tyr Ala Met His
1               5

<210> SEQ ID NO 104
<211> LENGTH: 17
<212> TYPE: PRT
<213> ORGANISM: human

<400> SEQUENCE: 104

Gly Ile Asn Trp Asn Gly Gly Ser Thr Asp Tyr Ala Asp Ser Val Glu
1               5                   10                  15
Gly

<210> SEQ ID NO 105
<211> LENGTH: 11
<212> TYPE: PRT
<213> ORGANISM: human

<400> SEQUENCE: 105

Asp Tyr Ala Asp Leu Gly Ser Gly Ser Asp Tyr
1               5                   10

```
<210> SEQ ID NO 106
<211> LENGTH: 13
<212> TYPE: PRT
<213> ORGANISM: human

<400> SEQUENCE: 106

Ser Gly Ser Arg Ser Asn Ile Gly Ser Asn Tyr Val His
1               5                   10

<210> SEQ ID NO 107
<211> LENGTH: 7
<212> TYPE: PRT
<213> ORGANISM: human

<400> SEQUENCE: 107

Arg Asn Asp Gln Arg Pro Ser
1               5

<210> SEQ ID NO 108
<211> LENGTH: 11
<212> TYPE: PRT
<213> ORGANISM: human

<400> SEQUENCE: 108

Ala Ser Trp Asp Asp Lys Met Ser Gly Arg Leu
1               5                   10

<210> SEQ ID NO 109
<211> LENGTH: 5
<212> TYPE: PRT
<213> ORGANISM: human

<400> SEQUENCE: 109

Ser Tyr Glu Met Asn
1               5

<210> SEQ ID NO 110
<211> LENGTH: 17
<212> TYPE: PRT
<213> ORGANISM: human

<400> SEQUENCE: 110

Tyr Ile Ser Ser Ser Gly Ser Thr Ile Tyr Tyr Ala Asp Ser Val Lys
1               5                   10                  15

Gly

<210> SEQ ID NO 111
<211> LENGTH: 17
<212> TYPE: PRT
<213> ORGANISM: human

<400> SEQUENCE: 111

His Ser Asn Tyr Asp Ile Leu Thr Gly Tyr Ser Thr Asp Ala Phe Asp
1               5                   10                  15

Ile

<210> SEQ ID NO 112
<211> LENGTH: 14
<212> TYPE: PRT
<213> ORGANISM: human

<400> SEQUENCE: 112

Thr Gly Thr Ser Ser Asp Ile Gly Phe Tyr Asp Ser Val Ser
1               5                   10
```

```
<210> SEQ ID NO 113
<211> LENGTH: 7
<212> TYPE: PRT
<213> ORGANISM: human

<400> SEQUENCE: 113

Asp Val Ser Asn Arg Pro Ser
1               5

<210> SEQ ID NO 114
<211> LENGTH: 11
<212> TYPE: PRT
<213> ORGANISM: human

<400> SEQUENCE: 114

Thr Ser Asn Thr Lys Thr Asn Thr Leu Tyr Val
1               5                   10

<210> SEQ ID NO 115
<211> LENGTH: 7
<212> TYPE: PRT
<213> ORGANISM: human

<400> SEQUENCE: 115

Arg Gly Asn Tyr Trp Trp Thr
1               5

<210> SEQ ID NO 116
<211> LENGTH: 16
<212> TYPE: PRT
<213> ORGANISM: human

<400> SEQUENCE: 116

Ser Val His Tyr Ser Gly Ser Thr Asn Tyr Asn Pro Ser Leu Lys Ser
1               5                   10                  15

<210> SEQ ID NO 117
<211> LENGTH: 11
<212> TYPE: PRT
<213> ORGANISM: human

<400> SEQUENCE: 117

Asp Ser Asp Tyr Gly Asp Tyr Tyr Phe Asp Tyr
1               5                   10

<210> SEQ ID NO 118
<211> LENGTH: 11
<212> TYPE: PRT
<213> ORGANISM: human

<400> SEQUENCE: 118

Gln Gly Asp Ser Leu Arg Ser Tyr Tyr Ala Ser
1               5                   10

<210> SEQ ID NO 119
<211> LENGTH: 7
<212> TYPE: PRT
<213> ORGANISM: human

<400> SEQUENCE: 119

Gly Lys Asn Asn Arg Pro Ser
1               5
```

```
<210> SEQ ID NO 120
<211> LENGTH: 11
<212> TYPE: PRT
<213> ORGANISM: human

<400> SEQUENCE: 120

Asn Ser Arg Asp Ser Ser Gly Asn His Val Val
1               5                   10

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: linkler

<400> SEQUENCE: 121

Gly Gly Gly Gly Ser Gly Gly Gly Gly Ser Gly Gly Gly Gly Ser
1               5                   10                  15

<210> SEQ ID NO 122
<211> LENGTH: 331
<212> TYPE: PRT
<213> ORGANISM: human

<400> SEQUENCE: 122

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255
```

```
Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330

<210> SEQ ID NO 123
<211> LENGTH: 106
<212> TYPE: PRT
<213> ORGANISM: human

<400> SEQUENCE: 123

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 124
<211> LENGTH: 19
<212> TYPE: PRT
<213> ORGANISM: human

<400> SEQUENCE: 124

Met Glu Phe Gly Leu Ser Trp Val Phe Leu Val Ala Ile Leu Lys Gly
1               5                   10                  15

Val Gln Cys

<210> SEQ ID NO 125
<211> LENGTH: 760
<212> TYPE: PRT
<213> ORGANISM: human

<400> SEQUENCE: 125

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
50                  55                  60

Ser Ile Cys Tyr Gly Thr Ile Ala Val Ile Val Phe Phe Leu Ile Gly
65                  70                  75                  80
```

```
Phe Met Ile Gly Tyr Leu Gly Tyr Cys Lys Gly Val Glu Pro Lys Thr
                85                  90                  95
Glu Cys Glu Arg Leu Ala Gly Thr Glu Ser Pro Val Arg Glu Glu Pro
            100                 105                 110
Gly Glu Asp Phe Pro Ala Ala Arg Arg Leu Tyr Trp Asp Asp Leu Lys
        115                 120                 125
Arg Lys Leu Ser Glu Lys Leu Asp Ser Thr Asp Phe Thr Gly Thr Ile
    130                 135                 140
Lys Leu Leu Asn Glu Asn Ser Tyr Val Pro Arg Glu Ala Gly Ser Gln
145                 150                 155                 160
Lys Asp Glu Asn Leu Ala Leu Tyr Val Glu Asn Gln Phe Arg Glu Phe
                165                 170                 175
Lys Leu Ser Lys Val Trp Arg Asp Gln His Phe Val Lys Ile Gln Val
            180                 185                 190
Lys Asp Ser Ala Gln Asn Ser Val Ile Val Asp Lys Asn Gly Arg
        195                 200                 205
Leu Val Tyr Leu Val Glu Asn Pro Gly Gly Tyr Val Ala Tyr Ser Lys
    210                 215                 220
Ala Ala Thr Val Thr Gly Lys Leu Val His Ala Asn Phe Gly Thr Lys
225                 230                 235                 240
Lys Asp Phe Glu Asp Leu Tyr Thr Pro Val Asn Gly Ser Ile Val Ile
                245                 250                 255
Val Arg Ala Gly Lys Ile Thr Phe Ala Glu Lys Val Ala Asn Ala Glu
            260                 265                 270
Ser Leu Asn Ala Ile Gly Val Leu Ile Tyr Met Asp Gln Thr Lys Phe
        275                 280                 285
Pro Ile Val Asn Ala Glu Leu Ser Phe Phe Gly His Ala His Leu Gly
    290                 295                 300
Thr Gly Asp Pro Tyr Thr Pro Gly Phe Pro Ser Phe Asn His Thr Gln
305                 310                 315                 320
Phe Pro Pro Ser Arg Ser Ser Gly Leu Pro Asn Ile Pro Val Gln Thr
                325                 330                 335
Ile Ser Arg Ala Ala Ala Glu Lys Leu Phe Gly Asn Met Glu Gly Asp
            340                 345                 350
Cys Pro Ser Asp Trp Lys Thr Asp Ser Thr Cys Arg Met Val Thr Ser
        355                 360                 365
Glu Ser Lys Asn Val Lys Leu Thr Val Ser Asn Val Leu Lys Glu Ile
    370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                405                 410                 415
Ala Lys Ser Gly Val Gly Thr Ala Leu Leu Leu Lys Leu Ala Gln Met
            420                 425                 430
Phe Ser Asp Met Val Leu Lys Asp Gly Phe Gln Pro Ser Arg Ser Ile
        435                 440                 445
Ile Phe Ala Ser Trp Ser Ala Gly Asp Phe Gly Ser Val Gly Ala Thr
    450                 455                 460
Glu Trp Leu Glu Gly Tyr Leu Ser Ser Leu His Leu Lys Ala Phe Thr
465                 470                 475                 480
Tyr Ile Asn Leu Asp Lys Ala Val Leu Gly Thr Ser Asn Phe Lys Val
                485                 490                 495
```

```
Ser Ala Ser Pro Leu Leu Tyr Thr Leu Ile Glu Lys Thr Met Gln Asn
            500                 505             510
Val Lys His Pro Val Thr Gly Gln Phe Leu Tyr Gln Asp Ser Asn Trp
        515                 520             525
Ala Ser Lys Val Glu Lys Leu Thr Leu Asp Asn Ala Ala Phe Pro Phe
        530             535             540
Leu Ala Tyr Ser Gly Ile Pro Ala Val Ser Phe Cys Phe Cys Glu Asp
545             550             555             560
Thr Asp Tyr Pro Tyr Leu Gly Thr Thr Met Asp Thr Tyr Lys Glu Leu
                565             570             575
Ile Glu Arg Ile Pro Glu Leu Asn Lys Val Ala Arg Ala Ala Ala Glu
            580             585             590
Val Ala Gly Gln Phe Val Ile Lys Leu Thr His Asp Val Glu Leu Asn
        595             600             605
Leu Asp Tyr Glu Arg Tyr Asn Ser Gln Leu Leu Ser Phe Val Arg Asp
        610             615             620
Leu Asn Gln Tyr Arg Ala Asp Ile Lys Glu Met Gly Leu Ser Leu Gln
625             630             635             640
Trp Leu Tyr Ser Ala Arg Gly Asp Phe Phe Arg Ala Thr Ser Arg Leu
                645             650             655
Thr Thr Asp Phe Gly Asn Ala Glu Lys Thr Asp Arg Phe Val Met Lys
                660             665             670
Lys Leu Asn Asp Arg Val Met Arg Val Glu Tyr His Phe Leu Ser Pro
            675             680             685
Tyr Val Ser Pro Lys Glu Ser Pro Phe Arg His Val Phe Trp Gly Ser
        690             695             700
Gly Ser His Thr Leu Pro Ala Leu Leu Glu Asn Leu Lys Leu Arg Lys
705             710             715             720
Gln Asn Asn Gly Ala Phe Asn Glu Thr Leu Phe Arg Asn Gln Leu Ala
                725             730             735
Leu Ala Thr Trp Thr Ile Gln Gly Ala Ala Asn Ala Leu Ser Gly Asp
            740             745             750
Val Trp Asp Ile Asp Asn Glu Phe
        755             760
```